US008557745B2

(12) United States Patent
Blank et al.

(10) Patent No.: US 8,557,745 B2
(45) Date of Patent: Oct. 15, 2013

(54) MARKERS AND METHODS FOR ASSESSING AND TREATING CROHN'S AND RELATED DISORDERS

(75) Inventors: Marion Blank, Malvern, PA (US); Gary Toedter, Radnor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 1365 days.

(21) Appl. No.: 12/125,426

(22) Filed: May 22, 2008

(65) Prior Publication Data

US 2009/0156418 A1 Jun. 18, 2009

Related U.S. Application Data

(60) Provisional application No. 60/939,502, filed on May 22, 2007.

(51) Int. Cl.
*C40B 30/04* (2006.01)
*C12Q 1/68* (2006.01)

(52) U.S. Cl.
USPC .................................................. 506/9; 435/6

(58) Field of Classification Search
None
See application file for complete search history.

(56) References Cited

U.S. PATENT DOCUMENTS

2001/0051344 A1* 12/2001 Shalon et al. .................... 435/6
2003/0215421 A1* 11/2003 McDonald et al. .......... 424/85.1
2004/0052791 A1 3/2004 Ehrhardt et al.
2004/0120923 A1 6/2004 Dinarello et al.
2006/0040329 A1 2/2006 Kelvin
2006/0216716 A1 9/2006 Saubermann et al.

FOREIGN PATENT DOCUMENTS

WO WO 01/29269 A2 4/2001
WO WO 2005/016962 A2 2/2005
WO WO 2005/110452 A2 11/2005
WO WO 2006/063133 A2 6/2006

OTHER PUBLICATIONS

Valid Concerns Editorial (Jan. 27, 2010) Nature vol. 463 pp. 401 to 402.*
Ladugger (2000) Circulation vol. 102 pp. 1221 to 1226.*
Metcalfe (Jun. 15, 2004) Journal of Clinical Oncology vol. 22 pp. 2328 to 2235.*
Lowe (2000) Thrombosis and Haemostasis vol. 84 pp. 553 to 558.*
Zimmern (May 24, 2007) Journal of Public Health vol. 1 pp. 1 to 5.*
Kroese (Dec. 2004) Genetics in Medicine vol. 6 pp. 475 to 480.*
Lucentini (Dec. 20, 2004) The Scientist vol. 18 pp. 20 to 23.*
Tainsky (Jul. 10, 2007) Biomarker Insights pp. 261 to 267.*
Miklos (May 2004) Nature Biotechnology vol. 22 pp. 615 to 621.*
Monteleone et al. (Jul. 1, 1999) Journal of Immunology vol. 163 pp. 143 to 147.*

(Continued)

*Primary Examiner* — Ardin Marschel
*Assistant Examiner* — Christian Boesen
(74) *Attorney, Agent, or Firm* — Eric Dichter

(57) ABSTRACT

A method for assessment of the suitability of and/or effectiveness of a target therapy for a gastrointestinal-related disorder, such as Crohn's disease, in a subject evaluates the presence, absence, and/or magnitude of expression of one or more genes in a 10-member gene panel in a sample. The method enables identification of the effectiveness of target therapies prior to or after starting a patient on such therapies.

9 Claims, 2 Drawing Sheets

(56) References Cited

OTHER PUBLICATIONS

Kader (Feb. 2005) American Journal of Gastroenterology vol. 100 pp. 414 to 423.*

PCT International Search Report dated Jan. 13, 2009.

Copy of Supplementary European Search Report dated Dec. 23, 2010.

Biomarkers Working Group, "Biomarkers and surrogate endpoints: Preferred definitions and conceptual framework," Clinical Pharmacology & Therapeutics, 69(3): 89-95 (2001).

Bousvaros, et al., "Elevated Serum Vascular Endothelial Growth Factor in Children and Young Adults with Crohn's Disease," Digestive Diseases & Sciences, 44(2): 424-430 (1999).

Dignass, et al., "Review article: the aetiopathogenesis of inflammatory bowel disease—immunology and repair mechanisms," Ailment Pharmacology Therapy, 20 (Suppl. 4): 9-17 (2004).

Farraye, et al., "Cytokine Stimulated CXC Chemokine Responses by Peripheral Blood Mononuclear Cells Reflect Levels of Disease Activity in Crohn's Disease," Gastroenterology, 126(4) Suppl. 2: A214-A215 (2004). Abstract Only.

Krueger, et al., "A Human Interleuken-12/23 Monoclonal Antibody for the Treatment of Psoriasis," The New England Journal of Medicine, 356: 580-592 (2007).

Louis, et al., "A Positive Response to Infliximab in Crohn's disease: Association with a Higher Systemic Inflammation Before Treatment But Not With -308 TNF Gene Polymorphism," Scandanavian Journal of Gastroenterology, 37(7): 818-824 (2002).

Mannon, et al., "Anti-Interleukin-12 Antibody for Active Crohn's Disease," The New England Journal of Medicine, 351:20-2069-2079 (2004).

Mascheretti, et al., "The role of pharmacogenomics in the prediction of efficacy of anti-TNF therapy in patients with Crohn's disease," Pharmacogenomics, 5(5): 479-486 (2004).

Peluso, et al., "Interleukin-12 and Th1 immune response in Crohn's disease: Pathogenetic relevance and therapeutic implication," World Journal of Gastroenterology, 12(35): 5606-5610 (2006).

Sandborn, et al., "Adalimumab for Maintenance Treatment of Crohn's Disease: Results of the CLASSIC II Trial," Gut, 56(9): 1232-1239 (2007).

Sher, et al., "Cytokines in Crohn's Colitis," American Journal of Surgery, 169(1): 133-136 (1995).

* cited by examiner

MARKERS AND METHODS FOR ASSESSING AND TREATING CROHN'S AND RELATED DISORDERS

CROSS-REFERENCE TO RELATED APPLICATIONS

This application claims the benefit of U.S. Provisional Application No. 60/939,502, filed May 22, 2007, the entire contents of which are incorporated herein by reference in its entirety.

FIELD OF THE INVENTION

The invention relates to the identification of expression profiles and the nucleic acids indicative of gastrointestinal-related disorders, such as Crohn's disease, and to the use of such expression profiles and nucleic acids in diagnosis of Crohn's disease and related diseases. The invention further relates to methods for identifying, using, and testing candidate agents and/or targets which modulate Crohn's disease.

BACKGROUND OF THE INVENTION

The treatment of Crohn's Disease with biologics presents a number of challenges. Determining which patient population to study, predicting which subjects will respond to treatment, and which subjects will lose response following treatment are issues that have significant impact upon treatment and clinical study design. Biomarkers may be useful in answering these questions.

Biomarkers are defined as "a characteristic that is objectively measured and evaluated as an indicator of normal biologic processes, pathogenic processes, or pharmacologic responses to a therapeutic intervention" (Biomarker Working Group, 2001). The definition of a biomarker has recently been further defined as proteins in which a change in the expression of may correlate with an increased risk of disease or progression, or predictive of a response of a disease to a given treatment.

Louis et al. (2002) used CRP (C-reactive protein) levels to identify which subjects with Crohn's Disease would response to the anti-TNFα antibody, infliximab. CRP levels in the responding subjects were significantly higher than in those subjects that did not respond to treatment. Schreiber et al. (2005) investigated the use of certolizumab pegol (a polyethylene-glycolated Fab' fragment of anti-TNFα in Crohn's disease. They found that subjects could be stratified by CRP levels. Patients with CRP baseline levels greater than 10 mg/L showed a greater difference between active treatment and placebo due to a lower placebo response rate than those patients with CRP levels of less than 10 mg/L.

Sher et al. (1995) examined the expression of IL-1β, IL-2, IL-6 and IL-8 in the involved and uninvolved colonic segments of subjects with Crohn's Disease, as compared with normal colon. It was found that both IL-1β and IL-8 were expressed significantly higher in the diseased colon than the normal colon.

Kader et al. (2005) used protein microarray to examine the serum cytokine levels of pediatric patients with Crohn's Disease and ulcerative colitis. It was found that thirteen cytokines, when used together in a classification matrix, were able to distinguish active Crohn's Disease from disease in remission. The cytokines identified were BDNF, I309, IL-17, MCP-1, MPIF-1, PLGF, SCD23, TARC, TRAIL, UPAR, IL-12p40, IL-7, and TGFβ1.

Kucharzik T, et al (1995) found that IL-10 is elevated in serum of patients with active CD and UC, which suggested that IL-10 has role in the inflammatory processes of IBD. Bousvarous (1999) measured VEGF levels in children and adolescents with Crohn's Disease. It was found that VEGF levels were significantly higher in patients with Crohn's disease than in ulcerative colitis or control patients. The serum VEGF levels correlated with disease activity, with concentrations being elevated in patients with moderate or severe Crohn's disease and ulcerative colitis.

A review of the pathogenesis of inflammatory bowel disease (Dignass 2004) listed a number of cytokines that play a role in wound healing in the gastrointestinal tract. Lesions in the lining of the bowel characterize Crohn's Disease, and resolution of the disease by wound healing is of importance. Included in the list are cytokines that stimulate migration (TGFa, TGFb, EGF, FGF, IL-2) and inflammation (IL-1, TNFα, IL-6), and suppress inflammation (TGFβ, IL-4, IL-10).

In a recent study of the effect of anti-IL-12 (ABT-874; Mannon 2004), peripheral blood lymphocytes obtained from the nine study subjects before and after treatment were stimulated in vitro, and the release of cytokines by the lymphocytes measured by ELISA. The results showed that the secretion of IL-12, TNFα, IL-6, and interferon-γ were significantly reduced in the anti-IL12 treated subjects.

The studies cited above have utilized biomarkers to define the response of subjects with Crohn's Disease to infliximab and other biologics, or to classify patients according to the severity of their disease. In the paper related to Crohn's Disease and anti-IL-12, the biomarkers were expressed by cultured cells, but not detected in serum or plasma. To enhance clinical usefulness, the biomarkers are detected in serum or plasma.

Microarray technology is a powerful tool since it enables analysis of the expression of thousands of genes simultaneously and can also be automated allowing for a high-throughput format. In diseases associated with complex host functions, such as those known as immune mediated inflammatory diseases, such as Crohn's, microarray results can provide a gene expression profile that can be of utility in designing new approaches to disease diagnosis and management. These approaches also serve to identify novel genes and annotating genes of unknown function heretofore unassociated with the disease or condition.

Gene expression can be modulated in several different ways, including by the use of siRNAs, shRNAs, antisense molecules and DNAzymes. SiRNAs and shRNAs both work via the RNAi pathway and have been successfully used to suppress the expression of genes. RNAi was first discovered in worms and the phenomenon of gene silencing related to dsRNA was first reported in plants by Fire and Mello and is thought to be a way for plant cells to combat infection with RNA viruses. In this pathway, the long dsRNA viral product is processed into smaller fragments of 21-25 bp in length by a DICER-like enzyme and then the double-stranded molecule is unwound and loaded into the RNA induced silencing complex (RISC). A similar pathway has been identified in mammalian cells with the notable difference that the dsRNA molecules must be smaller than 30 bp in length in order to avoid the induction of the so-called interferon response, which is not gene specific and leads to the global shut down of protein synthesis in the cell.

Synthetic siRNAs have been successfully designed to selectively target a single gene and can be delivered to cells in vitro or in vivo. ShRNAs are the DNA equivalents of siRNA molecules and have the advantage of being incorporated into a cells' genome where they are replicated during every mitotic cycle.

DNAzymes have also been used to modulate gene expression. DNAzymes are catalytic DNA molecules that cleave single-stranded RNA. They are highly selective for the target RNA sequence and as such can be used to down-regulate specific genes through targeting of the messenger RNA.

Accordingly, there is a need to identify and characterize new gene markers relevant from serum or plasma useful in developing methods for diagnosing and treating immune-mediated inflammatory disorders, such as Crohn's disease, as well as other diseases and conditions, and a method for predicting how a patient would respond to a therapeutic intervention.

SUMMARY OF THE INVENTION

The present invention relates to a method of diagnosing and/or treating Crohn's disease and/or related diseases or disorders and predicting the suitability of candidate agents for treatment. The present invention includes the discovery of particular genes of interest, and a panel of 10 genes that have modified expression levels in patients responsive to treatment for Crohn's disease (effective in reducing the symptoms of Crohn's disease) versus patients nonresponsive to treatment or placebo treated patients. The modified expression levels constitute a profile that can serve as a biomarker profile predictive of a patient's responsiveness to treatment and/or provide preferred dosage routes.

In another embodiment, the present invention use the gene panel in a method of assessing the effectiveness of candidate agents for treatment of Crohn's disease or related disorders, for example, at early time points of treatment where the effectiveness of treatment may not be measurable by symptoms or traditional disease characteristics.

In a particular embodiment, the present invention comprises a method of predicting the suitability of a treatment for Crohn's disease based on the pattern of gene expression of one or more of the ten genes which constitute the profile prior to treatment. One or more of these genes may be from a category of genes, such as cytokines, chemokines, proteins involved in extracellular matrix remodeling, angiogenesis associated growth factors, cell adhesion molecules, and myeloperoxidases, and the like. In a typical embodiment, the cell specimen expresses at least two expression profile genes. The profile genes may show an increase or decrease.

In addition, the present invention comprises a method of identifying subjects with Crohn's disease and/or related diseases or disorders that are candidates for treatment with a particular therapeutic agent by evaluating their expression profile of one or more genes of the panel.

In a further embodiment, the Crohn's disease-related gene profile is used to create an array-based method for prognostic or diagnostic purposes, the method comprising:

(a) preparing a representative mixture of nucleic acids from a specimen obtained from a patient and causing said sample nucleic acids in the mixture to be labeled with a detectable marker;

(b) contacting a sample with an array comprising a plurality of nucleic acid segments, wherein each nucleic acid segment is immobilized to a discrete and known address on a substrate surface wherein the panel of Crohn's disease-related biomarkers is identified as a feature of the array by address, the array further comprises at least one calibration nucleic acid at a known address on the substrate, and contacting is performed under conditions in which a sample nucleic acid specifically may bind to the nucleic acid segment immobilized on the arrays;

(c) performing a statistical comparison of all test samples from treated patients and a reference standard; and (d) comparing the pattern of intensity changes in features for the test sample to the pattern of intensity changes for those features which are members of the Crohn's disease-related gene profile with historical patterns for samples taken from patients responsive to treatment with an anti-IL-12 antibody.

Optionally, statistical analysis is performed on the changes in levels of members of the gene panel to evaluate the significance of these changes and to identify which members are meaningful members of the panel.

In an alternative embodiment, the present invention comprises a kit for predicting the suitability of candidate agents for treating Crohn's disease and/or related diseases or disorders based on the pattern of gene expression.

The present invention further provides any invention described herein.

DETAILED DESCRIPTION OF THE INVENTION

Definitions

Figure 1:
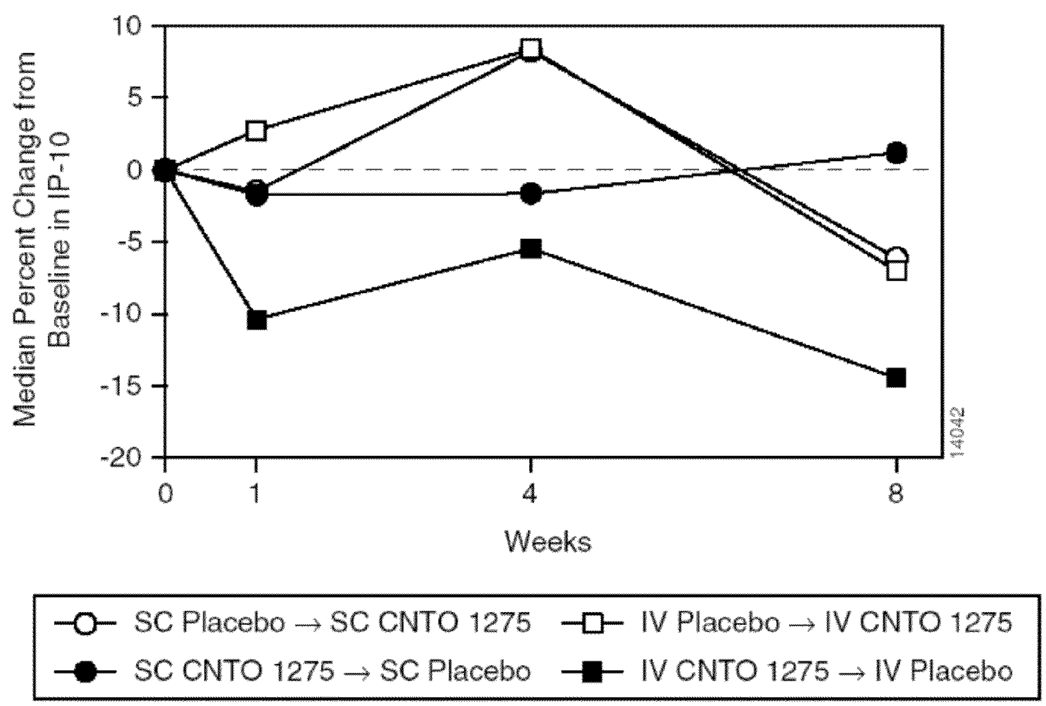
FIG. 1 shows the effect of IL-12 p40 treatment on serum expression of IP-10. IP-10 in serum was measured at Week 0 prior to the infusion of IL-12p40. Additional serum samples, obtained at Weeks 2, 4, and 8 were also tested for the effect of treatment on the expression of IP-10.
Figure 2:
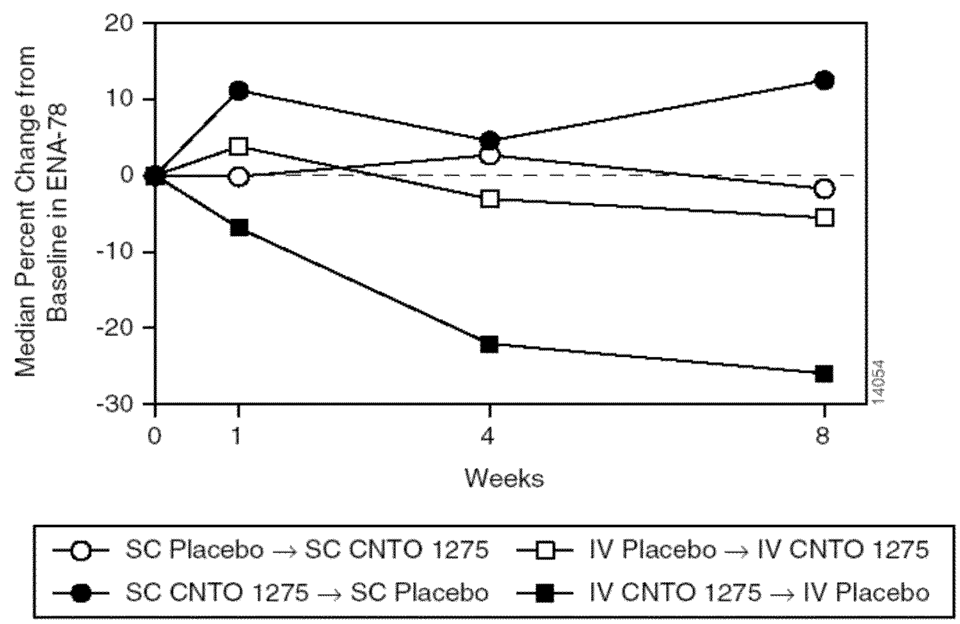
FIG. 2 shows the effect of IL-12p40 treatment on ENA-78 expression in serum. IP-10 in serum was measured at Week 0 prior to the infusion of IL-12p40. Additional serum samples, obtained at Weeks 2, 4, and 8 were also tested for the effect of treatment on the expression of IP-10.

The following definitions are set forth to illustrate and define the meaning and scope of various terms used to describe the invention herein.

An "activity," a biological activity, and a functional activity of a polypeptide refers to an activity exerted by a gene of the Crohn's disease-related gene panel in response to its specific interaction with another protein or molecule as determined in vivo, in situ, or in vitro, according to standard techniques. Such activities can be a direct activity, such as an association with or an enzymatic activity on a second protein, or an indirect activity, such as a cellular process mediated by interaction of the protein with a second protein or a series of interactions as in intracellular signaling or the coagulation cascade.

An "antibody" includes any polypeptide or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion, fragment or variant thereof. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. For example, antibody fragments include, but are not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, and single domain antibodies (e.g., $V_H$ or $V_L$), are encompassed by the invention (see, e.g., Colligan, et al., eds., Current Protocols in Immunology, John Wiley & Sons, Inc., NY (1994-2001); Colligan et al., Current Protocols in Polypeptide Science, John Wiley & Sons, NY (1997-2001)).

The terms "array" or "microarray" or "biochip" or "chip" as used herein refer to articles of manufacture or devices comprising a plurality of immobilized target elements, each target element comprising a "clone," "feature," "spot" or defined area comprising a particular composition, such as a biological molecule, e.g., a nucleic acid molecule or polypeptide, immobilized to a solid surface, as discussed in further detail, below.

"Complement of" or "complementary to" a nucleic acid sequence of the invention refers to a polynucleotide molecule having a complementary base sequence and reverse orientation as compared to a first polynucleotide.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.).

The terms "specifically hybridize to," "hybridizing specifically to," "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence; and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. Alternative hybridization conditions that can be used to practice the invention are described in detail, below. In alternative aspects, the hybridization and/or wash conditions are carried out under moderate conditions, stringent conditions and very stringent conditions, as described in further detail, below. Alternative wash conditions are also used in different aspects, as described in further detail, herein.

The phrases "labeled biological molecule" or "labeled with a detectable composition" or "labeled with a detectable moiety" as used herein refer to a biological molecule, e.g., a nucleic acid, comprising a detectable composition, i.e., a label, as described in detail, below. The label can also be another biological molecule, as a nucleic acid, e.g., a nucleic acid in the form of a stem-loop structure as a "molecular beacon," as described below. This includes incorporation of labeled bases (or, bases which can bind to a detectable label) into the nucleic acid by, e.g., nick translation, random primer extension, amplification with degenerate primers, and the like. Any label can be used, e.g., chemiluminescent labels, radiolabels, enzymatic labels and the like. The label can be detectable by any means, e.g., visual, spectroscopic, photochemical, biochemical, immunochemical, physical, chemical and/or chemiluminescent detection. The invention can use arrays comprising immobilized nucleic acids comprising detectable labels.

The term "nucleic acid" as used herein refers to a deoxyribonucleotide (DNA) or ribonucleotide (RNA) in either single- or double-stranded form. The term encompasses nucleic acids containing known analogues of natural nucleotides. The term nucleic acid is used interchangeably with gene, DNA, RNA, cDNA, mRNA, oligonucleotide primer, probe and amplification product. The term also encompasses DNA backbone analogues, such as phosphodiester, phosphorothioate, phosphorod ithioate, methyl phosphonate, phosphoramidate, alkyl phosphotriester, sulfamate, 3'-thioacetal, methylene (methylimino), 3'-N-carbamate, morpholino carbamate, and peptide nucleic acids (PNAs).

The terms "sample" or "sample of nucleic acids" as used herein refer to a sample comprising a DNA or RNA, or nucleic acid representative of DNA or RNA isolated from a natural source. A "sample of nucleic acids" is in a form suitable for hybridization (e.g., as a soluble aqueous solution) to another nucleic acid (e.g., immobilized probes). The sample nucleic acid may be isolated, cloned, or extracted from particular cells or tissues. The cell or tissue sample from which the nucleic acid sample is prepared is typically taken from a patient having or suspected of having UC or a related disease or condition. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves taken from patients or from cell cultures, cells from tissue culture and other media in which it may be desirable to detect the response to drug candidates. In some cases, the nucleic acids may be amplified using standard techniques such as PCR, prior to the hybridization. The probe an be produced from and collectively can be representative of a source of nucleic acids from one or more particular (pre-selected) portions of, e.g., a collection of polymerase chain reaction (PCR) amplification products, substantially an entire chromosome or a chromosome fragment, or substantially an entire genome, e.g., as a collection of clones, e.g., BACs, PACs, YACs, and the like (see below).

"Nucleic acids" are polymers of nucleotides, wherein a nucleotide comprises a base linked to a sugar which sugars are in turn linked one to another by an interceding at least bivalent molecule, such as phosphoric acid. In naturally occurring nucleic acids, the sugar is either 2'-deoxyribose (DNA) or ribose (RNA). Unnatural poly- or oligonucleotides contain modified bases, sugars, or linking molecules, but are generally understood to mimic the complementary nature of the naturally occurring nucleic acids after which they are designed. An example of an unnatural oligonucleotide is an antisense molecule composition that has a phosphorothioate backbone. An "oligonucleotide" generally refers to a nucleic acid molecule having less than 30 nucleotides.

The term "profile" means a pattern and relates to the magnitude and direction of change of a number of features. The profile may be interpreted stringently, i.e., where the variation in the magnitude and/or number of features within the profile displaying the characteristic is substantially similar to a reference profile or it may be interpreted less stringently, for example, by requiring a trend rather than an absolute match of all or a subset of feature characteristics.

The terms "protein," "polypeptide," and "peptide" include "analogs," or "conservative variants" and "mimetics" or "peptidomimetics" with structures and activity that substantially correspond to the polypeptide from which the variant was derived, as discussed in detail above.

A "polypeptide" is a polymer of amino acid residues joined by peptide bonds, and a peptide generally refers to amino acid polymers of 12 or less residues. Peptide bonds can be produced naturally as directed by the nucleic acid template or synthetically by methods well known in the art.

A "protein" is a macromolecule comprising one or more polypeptide chains. A protein may further comprise substituent groups attached to the side groups of the amino acids not involved in formation of the peptide bonds. Typically, proteins formed by eukaryotic cell expression also contain carbohydrates. Proteins are defined herein in terms of their amino acid sequence or backbone and substituents are not specified, whether known or not.

The term "receptor" denotes a molecule having the ability to affect biological activity, in e.g., a cell, as a result of interaction with a specific ligand or binding partner. Cell membrane bound receptors are characterized by an extracellular ligand-binding domain, one or more membrane spanning or transmembrane domains, and an intracellular effector domain that is typically involved in signal transduction. Ligand binding to cell membrane receptors causes changes in the extracellular domain that are communicated across the cell membrane, direct or indirect interaction with one or more intracellular proteins, and alters cellular properties, such as enzyme activity, cell shape, or gene expression profile. Receptors may also be untethered to the cell surface and may be cytosolic, nuclear, or released from the cell altogether. Non-cell associated receptors are termed soluble receptors or ligands.

| Biomarker Abbreviation | Full Name |
|---|---|
| BDNF | Brain Derived Neutropic Factor |
| CRP | C-reactive Protein |
| EGF | Epidermal growth factor |
| ENA-78 | Epithelial cell-derived protein 78/CXCL5 |
| FGF | Fibroblast growth factor |
| FGFbasic | Fibroblast growth factor basic |
| I309 | N/A |
| ICAM-1 | Intercellular adhesion molecule 1 |
| IFNγ | Interferon gamma |
| IL-1β | Interleukin 1 beta |
| IL-10 | Interleukin 10 |
| IL-12p40 | Interleukin 12 p40 subunit |
| IL-13 | Interleukin 13 |
| IL-17 | Interleukin 17 |
| IL-1ra | Interleukin 1 receptor agonist |
| IL-2 | Interleukin 2 |
| IL-4 | Interleukin 4 |
| IL-6 | Interleukin 6 |
| IL-7 | Interleukin 7 |
| IL-8 | Interleukin 8 |

-continued

| Biomarker Abbreviation | Full Name |
|---|---|
| IP-10 | interferon-gamma inducible protein 10 kDa/CXCL10 |
| MCP-1 | Monocyte chemotactic protein 1/CCL2 |
| MIP-1β | macrophage inflammatory protein beta |
| MMP-3 | matrix metalloproteinase 3 |
| MMP-9 | matrix metalloproteinase 9 |
| MPO | myeloperoxidase |
| PLGF | placenta growth factor |
| RANTES | CCL5, Regulated upon Activation, Normal T cell Expressed and Secreted |
| TARC | Thymus and activation-regulated chemokine/CCL17 |
| TGFβ1 | Transforming growth factor beta 1 |
| TGFa | Transforming growth factor alpha |
| TGFb | Transforming growth factor beta |
| TIMP-1 | Tissue inhibitor of matrix metalloproteinase 1 |
| TNFα | Tumor necrosis factor alpha |
| TRAIL | Apo2L/TNF-related apoptosis-inducing ligand |
| UPAR | urokinase-type plasminogen activator |
| VEGF | vascular endothelial growth factor |

All publications or patents cited herein are entirely incorporated herein by reference, whether or not specifically designated accordingly, as they show the state of the art at the time of the present invention and/or provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY (1997-2001).

Gene Panel Identification and Validation

The present invention provides novel methods for screening for compositions which modulate the symptoms of Crohn's disease, particularly the mucosal layer of the rectum and all or part of the colon. By "Crohn's disease" or grammatical equivalents as used herein, is meant a disease state or condition which is marked by chronic diarrhea, rectal bleeding, fever, crampy abdominal pain, granulomatous inflammation, and fistula formation, as a result of chronic inflammation of the intestinal wall.

In one aspect, the expression levels of genes are determined in different patient samples for which diagnosis information is desired, to provide expression profiles. An expression profile of a particular sample is essentially a "fingerprint" of the state of the sample; while two states may have any particular gene similarly expressed, the evaluation of a number of genes simultaneously allows the generation of a gene expression profile that is unique to the state of the patient sample. That is, normal tissue may be distinguished from lesion tissue and tissue from a treated patient may be distinguished from an untreated patient. By comparing expression profiles of tissue in different disease states that are known, information regarding which genes are important (including both up- and down-regulation of genes) in each of these states is obtained.

The identification of sequences (genes) that are differentially expressed in disease tissue allows the use of this information in a number of ways. For example, the evaluation of a particular treatment regime may be evaluated.

This may be done by making biochips comprising sets of the important disease genes, which can then be used in these screens. These methods can also be performed on the protein basis; that is, protein expression levels of the Crohn's disease-related gene product proteins can be evaluated for diagnostic purposes or to screen candidate agents. In addition, the nucleic acid sequences comprising the Crohn's disease-related gene profile can be used to measure whether a patient is likely to respond to a therapeutic prior to treatment.

Crohn's disease-related gene sequences can include both nucleic acid and amino acid sequences. In a preferred embodiment, the Crohn's disease-related gene sequences are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus, an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

Method of Practicing the Invention

The invention provides in silico, array-based methods relying on the relative amount of a binding molecule (e.g., nucleic acid sequence) in two or more samples. Also provided are computer-implemented methods for determining the relative amount of a binding molecule (e.g., nucleic acid sequence) in two or more samples and using the determined relative binding amount to predict responsiveness to a particular therapy, and monitor and enhance therapeutic treatment.

In practicing the methods of the invention, two or more samples of labeled biological molecules (e.g., nucleic acid) are applied to two or more arrays, where the arrays have substantially the same complement of immobilized binding molecule (e.g., immobilized nucleic acid capable of hybridizing to labeled sample nucleic acid). The two or more arrays are typically multiple copies of the same array. However, because each "spot," "clone" or "feature" on the array has similar biological molecules (e.g., nucleic acids of the same sequence) and the biological molecules (e.g., nucleic acid) in each spot is known, as is typical of nucleic acid and other arrays, it is not necessary that the multiple arrays used in the invention be identical in configuration it is only necessary that the position of each feature on the substrate be known, that is, have an address. Thus, in one aspect, multiple biological molecules (e.g., nucleic acid) in samples are comparatively bound to the array (e.g., hybridized simultaneously) and the information gathered is coded so that the results are based on the inherent properties of the feature (e.g., the nucleic acid sequence) and not it's position on the substrate.

Amplification of Nucleic Acids

Amplification using oligonucleotide primers can be used to generate nucleic acids used in the compositions and methods of the invention, to detect or measure levels of test or control samples hybridized to an array, and the like. The skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Hybridizing Nucleic Acids

In practicing the methods of the invention, test and control samples of nucleic acid are hybridized to immobilized probe nucleic acid, e.g., on arrays. In alternative aspects, the hybridization and/or wash conditions are carried out under moderate conditions, stringent conditions and very stringent conditions. An extensive guide to the hybridization of nucleic acids is found in, e.g., Sambrook Ausubel, Tijssen. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on an array or a filter in a Southern or northern blot is 42° C. using standard hybridization solutions (see, e.g., Sambrook), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook). Often, a high stringency wash is preceded by a medium or low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

In alternative aspects of the compositions and methods of the invention, e.g., in practicing comparative nucleic acid hybridization, such as comparative genomic hybridization (CGH) with arrays, the fluorescent dyes Cy3® and Cy5® are used to differentially label nucleic acid fragments from two samples, e.g., the array-immobilized nucleic acid versus the sample nucleic acid, or, nucleic acid generated from a control versus a test cell or tissue. Many commercial instruments are designed to accommodate the detection of these two dyes. To increase the stability of Cy5®, or fluors or other oxidation-sensitive compounds, antioxidants and free radical scavengers can be used in hybridization mixes, the hybridization and/or the wash solutions. Thus, Cy5® signals are dramatically increased and longer hybridization times are possible. See WO 0194630 A2 and U.S. Patent Application No. 20020006622.

To further increase the hybridization sensitivity, hybridization can be carried out in a controlled, unsaturated humidity environment; thus, hybridization efficiency is significantly improved if the humidity is not saturated. See WO 0194630 A2 and U.S. Patent Application No. 20020006622. The hybridization efficiency can be improved if the humidity is dynamically controlled, i.e., if the humidity changes during hybridization. Mass transfer will be facilitated in a dynamically balanced humidity environment. The humidity in the hybridization environment can be adjusted stepwise or continuously. Array devices comprising housings and controls that allow the operator to control the humidity during pre-hybridization, hybridization, wash and/or detection stages can be used. The device can have detection, control and memory components to allow pre-programming of the humidity and temperature controls (which are constant and precise or which flucturate), and other parameters during the entire procedural cycle, including pre-hybridization, hybridization, wash and detection steps. See WO 0194630 A2 and U.S. Patent Application No. 20020006622.

The methods of the invention can comprise hybridization conditions comprising osmotic fluctuation. Hybridization efficiency (i.e., time to equilibrium) can also be enhanced by a hybridization environment that comprises changing hyper-/hypo-tonicity, e.g., a solute gradient. A solute gradient is created in the device. For example, a low salt hybridization solution is placed on one side of the array hybridization chamber and a higher salt buffer is placed on the other side to generate a solute gradient in the chamber. See WO 0194630 A2 and U.S. Patent Application No. 20020006622.

Blocking the Ability of Repetitive Nucleic Acid Sequences to Hybridize

The methods of the invention can comprise a step of blocking the ability of repetitive nucleic acid sequences to hybridize (i.e., blocking "hybridization capacity") in the immobilized nucleic acid segments. The hybridization capacity of repetitive nucleic acid sequences in the sample nucleic acid sequences can be blocked by mixing sample nucleic acid sequences with unlabeled or alternatively labeled repetitive nucleic acid sequences. Sample nucleic acid sequences can be mixed with repetitive nucleic acid sequences before the step of contacting with the array-immobilized nucleic acid segments. Blocking sequences are for example, Cot-1 DNA, salmon sperm DNA, or specific repetitive genomic sequences. The repetitive nucleic acid sequences can be unlabeled. A number of methods for removing and/or disabling the hybridization capacity of repetitive sequences using, e.g., Cot-1 are known; see, e.g., Craig (1997) Hum. Genet. 100: 472-476; WO 93/18186. Repetitive DNA sequences can be removed from library probes by means of magnetic purification and affinity PCR, see, e.g., Rauch (2000) J. Biochem. Biophys. Methods 44:59-72.

Arrays are generically a plurality of target elements immobilized onto the surface of the plate as defined "spots" or "clusters," or "features," with each target element comprising one or more biological molecules (e.g., nucleic acids or polypeptides) immobilized to a solid surface for specific binding (e.g., hybridization) to a molecule in a sample. The immobilized nucleic acids can contain sequences from specific messages (e.g., as cDNA libraries) or genes (e.g., genomic libraries), including a human genome. Other target elements can contain reference sequences and the like. The biological molecules of the arrays may be arranged on the solid surface at different sizes and different densities. The densities of the biological molecules in a cluster and the number of clusters on the array will depend upon a number of factors, such as the nature of the label, the solid support, the degree of hydrophobicity of the substrate surface, and the like. Each feature may comprise substantially the same biological molecule (e.g., nucleic acid), or, a mixture of biological molecules (e.g., nucleic acids of different lengths and/or sequences). Thus, for example, a feature may contain more than one copy of a cloned piece of DNA, and each copy may be broken into fragments of different lengths.

Array substrate surfaces onto which biological molecules (e.g., nucleic acids) are immobilized can include nitrocellulose, glass, quartz, fused silica, plastics and the like, as discussed further, below. The compositions and methods of the invention can incorporate in whole or in part designs of arrays, and associated components and methods, as described, e.g., in U.S. Pat. Nos. 6,344,316; 6,197,503; 6,174,684; 6,159,685; 6,156,501; 6,093,370; 6,087,112; 6,087,103; 6,087,102; 6,083,697; 6,080,585; 6,054,270; 6,048,695; 6,045,996; 6,022,963; 6,013,440; 5,959,098; 5,856,174; 5,843,655; 5,837,832; 5,770,456; 5,723,320; 5,700,637; 5,695,940; 5,556,752; 5,143,854; see also, e.g., WO 99/51773; WO 99/09217; WO 97/46313; WO 96/17958; WO 89/10977; see also, e.g., Johnston (1998) Curr. Biol. 8:R171-174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32; Epstein (2000) Current Opinion in Biotech. 11:36-41; Mendoza (1999 Biotechniques 27: 778-788; Lueking (1999) Anal. Biochem. 270:103-111; Davies (1999) Biotechniques 27:1258-1261.

Substrate Surfaces

Substrate surfaces that can be used in the compositions and methods of the invention include, for example, glass (see, e.g., U.S. Pat. No. 5,843,767), ceramics, and quartz. The arrays can have substrate surfaces of a rigid, semi-rigid or flexible material. The substrate surface can be flat or planar, be shaped as wells, raised regions, etched trenches, pores, beads, filaments, or the like. Substrate surfaces can also comprise various materials such as nitrocellulose, paper, crystalline substrates (e.g., gallium arsenide), metals, metalloids, polacryloylmorpholide, various plastics and plastic copolymers, Nylon®, Teflon®, polyethylene, polypropylene, latex, polymethacrylate, poly(ethylene terephthalate), rayon, nylon, poly(vinyl butyrate), and cellulose acetate. The substrates may be coated and the substrate and the coating may be functionalized to, e.g., enable conjugation to an amine.

Arrays Comprising Calibration Sequences

The invention comtemplates the use of arrays comprising immobilized calibration sequences for normalizing the results of array-based hybridization reactions, and methods for using these calibration sequences, e.g., to determine the copy number of a calibration sequence to "normalize" or "calibrate" ratio profiles. The calibration sequences can be substantially the same as a unique sequence in an immobilized nucleic acid sequence on an array. For example, a "marker" sequence from each "spot" or "biosite" on an array (which is present only on that spot, making it a "marker" for that spot) is represented by a corresponding sequence on one or more "control" or "calibration" spot(s).

The "control spots" or "calibration spots" are used for "normalization" to provide information that is reliable and repeatable. Control spots can provide a consistent result independent of the labeled sample hybridized to the array (or a labeled binding molecule from a sample). The control spots can be used to generate a "normalization" or "calibration" curve to offset possible intensity errors between the two arrays (or more) used in the in silico, array-based methods of the invention.

One method of generating a control on the array would be to use an equimolar mixture of all the biological molecules (e.g., nucleic acid sequences) spotted on the array and generating a single spot. This single spot would have equal amounts of the biological molecules (e.g., nucleic acid sequences) from all the other spots on the array. Multiple control spots can be generated by varying the concentration of the equimolar mixture.

Samples and Specimens

The sample nucleic acid may be isolated, cloned, or extracted from particular cells, tissues, or other specimens. The cell or tissue sample from which the nucleic acid sample is prepared is typically taken from a patient having or suspected of having Crohn's disease or a related condition. Methods of isolating cell and tissue samples are well known to those of skill in the art and include, but are not limited to, aspirations, tissue sections, needle biopsies, and the like. Frequently, the sample will be a "clinical sample" which is a sample derived from a patient, including whole blood, serum, plasma, or sections of tissues, such as frozen sections or paraffin sections taken for histological purposes. The sample can also be derived from supernatants (of cells) or the cells themselves taken from patients or from cell cultures, cells from tissue culture and other media in which it may be desirable to detect the response to drug candidates. In some cases, the nucleic acids may be amplified using standard techniques such as PCR, prior to the hybridization.

In one embodiment, the present invention is a pre-treatment method of predicting disease regression or resolution. The method includes (1) taking a colon biopsy or other specimen from an individual diagnosed with Crohn's disease or a related disease or disorder, (2) measuring the expression levels of the profile genes of the panel, (3) comparing the pre-treatment expression level of the genes with a pre-treatment reference profile from treatment responders, and (4) predicting treatment response by monitoring the expression levels of the gene panel.

Methods of Assessing Biomarker Utililty

The prognostic utility of the present biomarker gene panel for assessing a patient's response to treatment or prognosis of disease can be validated by using other means for assessing a patient's state of disease. For example, gross measurement of disease may be assessed and recorded by certain imaging methods, such as but not limited to: imaging by photographic, radiometric, or magnetic resonance technology. General indices of health or disease further include serum or blood composition (protein, liver enzymes, pH, electrolytes, red cell volume, hematocrit, hemoglobin, or specific protein). However, in some diseases, the etiology is still poorly understood. Crohn's disease is an example of one such disease.

Patient Assessment and Monitoring

Some of the genes in the panel belong to classes of genes that have been reported to be aberrantly expressed in Crohn's disease patients previously. The expression patterns of the genes over the course of treatment have not been studied in the treatment of Crohn's disease, and none has been identified as having predictive value. The panel of gene expression biomarkers disclosed herein permits the generation of methods for rapid and reliable prediction, diagnostic tools that predict the clinical outcome of a Crohn's disease trial, or prognostic tools for tracking the efficacy of Crohn's disease therapy. Prognostic methods based on detecting these genes in a sample are provided. These compositions may be used, for example, in connection with the diagnosis, prevention and treatment of a range of immune-mediated inflammatory diseases.

Therapeutic Agents

Antagonists

As used herein, the term "antagonists" refer to substances which inhibit or neutralize the biologic activity of the gene product of the Crohn's disease-related gene panel of the invention. Such antagonists accomplish this effect in a variety of ways. One class of antagonists will bind to the gene product protein with sufficient affinity and specificity to neutralize the biologic effects of the protein. Included in this class of molecules are antibodies and antibody fragments (such as, for example, F(ab) or $F(ab')_2$ molecules). Another class of antagonists comprises fragments of the gene product protein, muteins or small organic molecules, i.e., peptidomimetics, that will bind to the cognate binding partners or ligands of the gene product, thereby inhibiting the biologic activity of the specific interaction of the gene product with its cognate ligand or receptor. The Crohn's disease-related gene antagonist may be of any of these classes as long as it is a substance that inhibits at least one biological activity of the gene product.

Antagonists include antibodies directed to one or more regions of the gene product protein or fragments thereof, antibodies directed to the cognate ligand or receptor, and partial peptides of the gene product or its cognate ligand which inhibit at least one biological activity of the gene product. Another class of antagonists includes siRNAs, shRNAs, antisense molecules and DNAzymes targeting the gene sequence as known in the art are disclosed herein.

Suitable antibodies include those that compete for binding to Crohn's disease-related gene products with monoclonal antibodies that block Crohn's disease-related gene product activation or prevent Crohn's disease-related gene product binding to its cognate ligand, or prevent Crohn's disease-related gene product signalling.

A therapeutic targeting the inducer of the Crohn's disease-related gene product may provide better chances of success. Gene expression can be modulated in several different ways including by the use of siRNAs, shRNAs, antisense molecules and DNAzymes. Synthetic siRNAs, shRNAs, and DNAzymes can be designed to specifically target one or more genes and they can easily be delivered to cells in vitro or in vivo.

The present invention encompasses antisense nucleic acid molecules, i.e., molecules that are complementary to a sense nucleic acid encoding a Crohn's disease-related gene product polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a Crohn's disease-related gene product polypeptide. The non-coding regions ("5' and 3' untranslated regions") are the 5' and 3' sequences that flank the coding region and are not translated into amino acids.

The invention also provides chimeric or fusion proteins. As used herein, a "chimeric protein" or "fusion protein" comprises all or part (preferably biologically active) of a Crohn's disease-related gene product polypeptide operably linked to a heterologous polypeptide (i.e., a polypeptide other than the same UC-related gene product polypeptide). Within the fusion protein, the term "operably linked" is intended to indicate that the Crohn's disease-related gene product polypeptide and the heterologous polypeptide are fused in-frame to each other. The heterologous polypeptide can be fused to the amino-terminus or the carboxyl-terminus of the Crohn's disease-related gene product polypeptide. In another embodiment, a Crohn's disease-related gene product polypeptide or a domain or active fragment thereof can be fused with a heterologous protein sequence or fragment thereof to form a chimeric protein, where the polypeptides, domains or fragments are not fused end to end but are interposed within the heterologous protein framework.

In yet another embodiment, the fusion protein is an immunoglobulin fusion protein in which all or part of a Crohn's disease-related gene product polypeptide is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a Crohn's disease-related gene product polypeptide. Inhibition of ligand/receptor interaction can be useful therapeutically, both for treating proliferative and differentiative disorders and for modulating (e.g., promoting or inhibiting) cell survival. A preferred embodiment of an immunoglobulin chimeric protein is a $C_H1$ domain-deleted immunoglobulin or MIMETIBODY™ construct having an active polypeptide fragment interposed within a modified framework region as taught in co-pending application PCT WO/04002417. Moreover, the immunoglobulin fusion proteins of the invention can be used as immunogens to produce antibodies directed against a Crohn's disease-related gene product polypeptide in a subject, to purify ligands and in screening assays to identify molecules that inhibit the interaction of receptors with ligands.

Compositions and Their Uses

In accordance with the invention, the neutralizing anti-Crohn's disease-related gene product antagonists, such as monoclonal antibodies, described herein can be used to inhibit Crohn's disease-related gene product activity. Additionally, such antagonists can be used to inhibit the pathogenesis of Crohn's disease and related inflammatory diseases amenable to such treatment, which may include, but are not limited to, rheumatic diseases. The individual to be treated may be any mammal and is preferably a primate, a companion animal which is a mammal and most preferably a human patient. The amount of antagonist administered will vary according to the purpose it is being used for and the method of administration.

The Crohn's disease-related gene antagonists may be administered by any number of methods that result in an effect in tissue in which pathological activity is desired to be prevented or halted. Further, the anti-Crohn's disease-related gene product antagonists need not be present locally to impart an effect on the Crohn's disease-related gene product activity, therefore, they may be administered wherever access to body compartments or fluids containing Crohn's disease-related gene product is achieved. In the case of inflamed, malignant, or otherwise compromised tissues, these methods may include direct application of a formulation containing the antagonists. Such methods include intravenous administration of a liquid composition, transdermal administration of a liquid or solid formulation, oral, topical administration, or interstitial or inter-operative administration. Administration may be affected by the implantation of a device whose primary function may not be as a drug delivery vehicle.

For antibodies, the preferred dosage is about 0.1 mg/kg to 100 mg/kg of body weight (generally about 10 mg/kg to 20 mg/kg). If the antibody is to act in the brain, a dosage of about 50 mg/kg to 100 mg/kg is usually appropriate. Generally, partially human antibodies and fully human antibodies have a longer half-life within the human body than other antibodies. Accordingly, the use of lower dosages and less frequent administration is often possible. Modifications, such as lipidation, can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The Crohn's disease-related gene product antagonist nucleic acid molecules can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Pharmacogenomics

Agents, or modulators that have a stimulatory or inhibitory effect on activity or expression of a Crohn's disease-related gene product polypeptide as identified by a screening assay described herein, can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a Crohn's disease-related gene product polypeptide, expression of a Crohn's disease-related gene product nucleic acid, or mutation content of a Crohn's disease-related gene product gene in an individual can be determined to thereby select an appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2): 254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism." These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a Crohn's disease-related gene product polypeptide, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

Methods of Treatment

The present invention provides for both prophylactic and therapeutic methods of treating a subject at risk of (or susceptible to) a disorder or having a disorder associated with aberrant expression or activity of a Crohn's disease-related gene product polypeptide and/or in which the Crohn's disease-related gene product polypeptide is involved.

The present invention provides a method for modulating or treating at least one Crohn's disease-related gene product related disease or condition, in a cell, tissue, organ, animal, or patient, as known in the art or as described herein, using at least one Crohn's disease-related gene product antagonist.

Compositions of Crohn's disease-related gene product antagonist may find therapeutic use in the treatment of Crohn's disease or related conditions, such as ulcerative colitis or other gastrointestinal disorders.

The present invention also provides a method for modulating or treating at least one gastrointestinal, immune related disease, in a cell, tissue, organ, animal, or patient including, but not limited to, at least one of gastric ulcer, inflammatory bowel disease, ulcerative colitis, Crohn's pathology, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

Disorders characterized by aberrant expression or activity of the Crohn's disease-related gene product polypeptides are further described elsewhere in this disclosure.

1. Prophylactic Methods

In one aspect, the invention provides a method for at least substantially preventing in a subject, a disease or condition associated with an aberrant expression or activity of a Crohn's disease-related gene product polypeptide, by administering to the subject an agent that modulates expression or at least one activity of the polypeptide. Subjects at risk for a disease that is caused or contributed to by aberrant expression or activity of a Crohn's disease-related gene product can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. The appropriate agent can be determined based on screening assays described herein.

2. Therapeutic Methods

Another aspect of the invention pertains to methods of modulating expression or activity of Crohn's disease-related gene or gene product for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. In another embodiment, the agent inhibits one or more of the biological activities of the Crohn's disease-related gene or gene product polypeptide. Examples of such inhibitory agents include antisense nucleic acid molecules and antibodies and other methods described herein. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a Crohn's disease-related gene product polypeptide. In one embodiment, the method involves administering an agent (e.g., an agent identified by a screening assay described herein), or combination of agents that modulate (e.g., up-regulates or down-regulates) expression or activity. Inhibition of activity is desirable in situations in which activity or expression is abnormally high or up-regulated and/or in which decreased activity is likely to have a beneficial effect.

While having described the invention in general terms, the embodiments of the invention will be further disclosed in the following examples which should not be construed as limiting the scope of the claims.

EXAMPLE 1

Serum samples were evaluated from 121 subjects enrolled in a clinical trial of Crohn's Disease subjects treated with the anti-IL-12/23 antibody CNTO 1275 (anti-IL-12p40 and anti-IL-23p40) at weeks 0, 1, 4, and 8. The trial assessed the treatment-related effects of CNTO 1275 on circulating serum proteins. Subjects were treated with either a single intravenous (IV) infusion of CNTO 1275, or a series of four subcutaneous (SC) injections.

The sera were analyzed for biomarkers using commercially available multiplex analysis (Pierce SearchLight, MesoScale Discovery). Multiplex analysis is a technique by which multiple, simultaneous EIA assays can be performed using a single serum sample. The analytical plex was manufactured by the vendor and validated at Centocor following selection of key markers of interest for this study. The markers that were tested (shown below in Tables 1A and 1B) were cytokines (IL-12p40, IFNγ, TNFα, IL-4, IL-1ra, IL-6, IL-8, IL-13), chemokines (IP-10, MCP-1, MIP-1β, ENA-78, RANTES), proteins involved in extracellular matrix remodeling (MMP-3, MMP-9, TIMP-1), angiogenesis associated growth factors (EGF, FGFbasic, VEGF), a cell adhesion molecule (ICAM-1), and myeloperoxidase (MPO).

The serum samples that were obtained from the subjects allowed a placebo-controlled evaluation of biomarker changes in response to CNTO 1275 treatment. Notable decreases in serum levels relative to placebo of IP-10, MCP-1, ENA-78, MMP-3, MMP-9, TIMP-1, TNFα, EGF, VEGF, IL-6, and MPO at week 1 were observed in Population 1 following a single CNTO1275 IV infusion relative to placebo. At weeks 4 and 8, the median percent change from baseline in serum levels of IP-10, TNFα, MMP-3, IL-6, and ENA-78 continued to distinguish CNTO1275 IV-treated patients from placebo.

In contrast, RANTES and IL-12p40 showed an increase in expression at week 1. The increased IL-12p40 levels in CNTO1275 IV and SC treated patients is consistent with biologically inactive IL-12p40 being bound to CNTO 1275. RANTES is chemotactic for T-cells, and plays a role in both promoting and controlling inflammation.

The decrease in expression at week 1 was also seen in CNTO 1275 SC treated subjects in VEGF, MPO, IL-6, EGF, and MMP-9. However, with these four cytokines, the median percent change was less than that seen with the IV treated subjects. The smaller response seen in SC treatment, combined with the fewer number of cytokines that were affected, may indicate that IV treatment can induce a cytokine response in less time than that of SC treatment.

At weeks 4 and 8, the median percent change from baseline in serum levels of IP-10, TNFα, MMP-3, IL-6, and ENA-78 continued to distinguish CNTO1275 IV-treated patients from placebo. The expression of the markers was reduced as compared with the placebo treated groups. The SC CNTO 1275 treatment groups did show a decreased expression, but generally was not as pronounced, and occurred at timepoints later that seen in the IV treated subjects.

TABLE 1A

Percent change from baseline for selected markers at weeks 1, 4, and 8. Population 1

| | | Week 1 | | Week 4 | | Week 8 | |
|---|---|---|---|---|---|---|---|
| SEQ ID NO | Treatment groups: | IV Placebo n = 26 | IV CNTO 1275 (4.5 mg/kg) n = 27 | IV Placebo n = 26 | IV CNTO 1275 (4.5 mg/kg) n = 27 | IV Placebo n = 26 | IV CNTO 1275 (4.5 mg/kg) n = 27 |
| 1 | IP-10 | 2.8 | −10.4 | 8.4 | −5.4 | −6.9 | −14.4 |
| 2 | MCP-1 | 6.4 | −8.5 | −9.3 | 3.8 | −5.4 | −9.2 |
| 3 | MMP-9 | 18.8 | −15.7 | 3.9 | 5.8 | −11.3 | −7.3 |
| 4 | TNFα | −1.6 | −14.2 | −8.2 | −8.9 | −4.9 | −15.4 |
| 5 | EGF | −2.0 | −46.3 | −34.9 | 2.9 | 9.0 | −1.7 |
| 6 | IL-6 | −15.1 | −51.4 | −22.4 | −46.1 | −7.8 | −41.6 |
| 7 | ENA-78 | 3.8 | −6.8 | −3.0 | −22.0 | −5.5 | −25.9 |
| 8 | MPO | −8.9 | −39.0 | −25.7 | −22.8 | −34.7 | −19.3 |
| 9 | MIP-1β | 1.6 | −5.7 | −8.5 | 1.8 | 10.7 | −14.8 |
| 10 | VEGF | 8.4 | −11.4 | −13.4 | −7.9 | −2.7 | −14.6 |

TABLE 1B

Percent change from baseline for selected markers at weeks 1, 4, and 8 Population 2

| Treatment groups: | Week 1 IV CNTO 1275 (4.5 mg/kg) n = 27 | Week 4 IV CNTO 1275 (4.5 mg/kg) n = 27 | Week 8 IV CNTO 1275 (4.5 mg/kg) n = 27 |
|---|---|---|---|
| IP-10 | −0.7 | −18.0 | −7.8 |
| MCP-1 | −5.1 | −11.4 | −9.6 |
| MMP-9 | −12.9 | 28.9 | −29.6 |
| TNFα | −7.7 | −24.6 | −15.5 |
| EGF | −48.4 | 22.7 | −1.6 |
| IL-6 | −33.5 | −26.5 | −75.0 |
| ENA-78 | −16.2 | −15.6 | −3.8 |
| MPO | −29.5 | −5.3 | −29.9 |
| MIP-1β | −14.2 | −9.8 | 6.3 |
| VEGF | −13.7 | −15.6 | −26.1 |

Initial statistical analysis of the serum biomarker results indicates that the baseline levels of IL-1, ICAM-1, IP-10, and VEGF are associated with a change in response to treatment. In addition, IL-1, ICAM-1, IL-6, IP-10, MCP-1, and VEGF changes at week 1 following treatment were significantly associated with the week 8 subject response to treatment.

The change in the expression of the serum markers seen in this study is consistent with the down regulation of inflammation by the CNTO 1275 treatment. The IV CNTO 1275 treatment group tended to show greater changes in cytokine expression at week 1 than the SC CNTO 1275 groups. The change in expression following treatment with CNTO 1275 supports the hypothesis that CNTO 1275 treatment can be of benefit to Crohn's Disease subjects.

Tables 2-7 below further demonstrate the change in members of the gene panel in response to treatement with the anti-IL-12 antibody CNTO 1275. Statistical analysis was performed for the individual genes in the panel. Markers with a p-value of less that 0.05 are considered to have changes in the expression of the marker that are significantly different from the changes seen in the placebo treated patients. Statistical analysis is performed for any combination of genes in the panel to determine p-values, etc.

TABLE 2

Population 1 CNTO 1275 SC treated subjects, p-values for median percent change from baseline, difference from placebo at weeks 1, 4, and 8, all subjects Wilcoxon rank-sum test

| Marker | Wk 1 SC CNTO 1275 p-Value (n = 25) | Wk 4 SC CNTO 1275 p-Value (n = 22) | Wk 8 SC CNTO 1275 p-Value (n = 23) |
|---|---|---|---|
| IP-10 | 0.0785[a] | 0.0785 | 0.6014[a] |
| MCP-1 | 0.5324[a] | 0.5324 | 0.5106 |
| MMP-9 | 0.4072[a] | 0.4072 | 0.8325 |
| TNFα | 0.0951 | 0.0951 | 0.4312 |
| EGF | 0.6950 | 0.1431 | 0.7070 |
| IL-6 | 0.0650 | 0.6878[b] | 0.1899[a] |
| ENA-78 | 0.2740 | 0.3345 | 0.2496 |
| MPO | 0.1373 | 0.9006 | 0.9251 |
| MIP-1β | 0.0946 | 0.5936 | 0.3354 |
| VEGF | 0.5358 | 0.1494 | 0.3473 |

[a]n = 22;
[b]n = 21

TABLE 3

Population 1 CNTO 1275 IV treated subjects, p-values for median percent change from baseline, difference from placebo at Weeks 1, 4, and 8, all subjects Wilcoxon rank-sum test

| Marker | Wk 1 IV CNTO 1275 p-Value (n = 25) | Wk 4 IV CNTO 1275 p-Value (n = 24) | Wk 8 IV CNTO 1275 p-Value (n = 21) |
|---|---|---|---|
| IP-10 | 0.1075 | 0.7666 | 0.4887 |
| MCP-1 | 0.0453 | 0.2483 | 0.6531 |
| MMP-9 | 0.1668 | 0.6053 | 0.6707 |
| TNFα | 0.1668 | 0.3388 | 0.5197 |
| EGF | 0.1668 | 0.1693 | 0.2291 |
| IL-6 | 0.0089 | 0.0694 | 0.0886 |
| ENA-78 | 0.2563 | 0.1159 | 0.1171 |
| MPO | 0.2081 | 0.9562 | 0.2485 |
| MIP-1β | 0.1935 | 0.4096 | 0.1552 |
| VEGF | 0.2156 | 0.7167 | 0.3133 |

TABLE 4

Spearman rank correlation between week 1 Biomarker Change and Change in CDAI at Week 8; All CNTO1275 SC Treated Subjects

| Inflammatory Molecule | Correlation Coefficient | p-Value |
|---|---|---|
| IP-10 | 0.293 | 0.174 |
| MCP-1 | 0.036 | 0.872 |
| MMP-9 | 0.271 | 0.211 |
| TNFα | 0.236 | 0.277 |
| EGF | −0.018 | 0.936 |
| IL-6 | −0.053 | 0.809 |
| ENA-78 | −0.260 | 0.231 |
| MPO | 0.291 | 0.179 |
| MIP-1β | 0.078 | 0.723 |
| VEGF | 0.064 | 0.771 |

n = 23 for all determinations

TABLE 5

Spearman rank correlation between Week 1 Biomarker Change and Change in CDAI at Week 8; All CNTO1275 IV Treated Subjects

| Inflammatory Molecule | Correlation Coefficient | p-Value |
|---|---|---|
| IP-10 | 0.264 | 0.224 |
| MCP-1 | 0.258 | 0.235 |
| MMP-9 | 0.153 | 0.485 |
| TNFα | 0.507 | 0.013 |
| EGF | 0.027 | 0.903 |
| IL-6 | 0.588 | 0.003 |
| ENA-78 | 0.107 | 0.628 |
| MPO | 0.161 | 0.463 |
| MIP-1β | 0.338 | 0.115 |
| VEGF | 0.197 | 0.360 |

n = 23 for all determinations

TABLE 6

Logistic regression between biomarker baseline value and response (≥100 CDAI) at Week 8 for infliximab experienced subjects in Population 1

| Biomarker | 1275 Treated subjects[a] | Placebo treated subjects[b] |
|---|---|---|
| IP-10 | 0.610 | 0.630 |
| MCP-1 | 0.045 | 0.284 |
| MMP-9 | 0.224 | 0.832 |
| TNFα | 0.711 | 0.309 |
| EGF | 0.814 | 0.265 |
| IL-6 | 0.719 | 0.645 |
| ENA-78 | 0.406 | 0.263 |
| MPO | 0.127 | 0.973 |
| MIP-1β | 0.904 | 0.262 |
| VEGF | 0.397 | 0.937 |

[a]p-value (association between marker and clinical response); n = 21
[b]n = 26

TABLE 7

Logistic regression between change from baseline at Week 1 and response (≥100 CDAI) at Week 8 for infliximab experienced subjects in Population 1.

| Biomarker | 1275 Treated subjects[a] | Placebo treated subjects[b] |
|---|---|---|
| IP-10 | 0.289 | 0.847 |
| MCP-1 | 0.040 | 0.645 |
| MMP-9 | 0.195 | 0.874 |
| TNFα | 0.919 | 0.166 |
| EGF | 0.946 | 0.310 |
| IL-6 | 0.377 | 0.747 |
| ENA-78 | 0.437 | 0.214 |
| MPO | 0.189 | 0.969 |
| MIP-1β | 0.956 | 0.729 |
| VEGF | 0.368 | 0.711 |

[a]p-value (association between marker and clinical response); n = 21
[b]n = 26

As an example, serum was obtained from patients who had been treated with CNTO 1275. A number of biomarkers in the serum samples were analyzed, and the change in the expression of the biomarkers one week after treatment was determined. This change in biomarker expression was then used to determine if the change in the biomarker expression correlated with the change in the severity of disease. The severity of disease was measured by the Crohn's Disease Activity Index (CDAI), a well-accepted measure of severity. It was found that the change in expression of TNFα and IL-6 had a statistically significant positive correlation with the change in the CDAI at Week 8. The decrease in the TNFα and IL-6 at one week predicted the response of the patients to the treatment.

Serum was obtained from patients who had previously received infliximab, but did not continue with the treatment. The baseline biomarker values were compared with the response of the patients to treatment eight weeks after they received their first treatment, using the CDAI to measure the severity of the disease. A biomarker (MCP-1) was shown to predict the response to treatment. Patients treated with a placebo did not show this predictive change in the marker.

In the same patients, the change in the biomarker at one week following treatment was compared with the response to treatment. Again, a biomarker (MCP-1) predicted the response of the patients at week 8. The biomarkers mentioned above are examples of the change in biomarkers that are predictive of patient response to treatment. It is expected that further analysis of serum samples from patients treated with anti-IL-12p40 will reveal additional inflammation-related markers that can be of use in predicting the response to treatment. The markers of use may be inflammatory cytokines, such as IL-8, or IL-1, inflammatory chemokines, such as ENA-78/CXCL5, RANTES, MIP-1β; Angiogenesis associated proteins (EGF, VEGF); Matrix metalloproteinase proteins, for example MMP-9, TIMP-1, MMP-3; TH-1 molecules (IFNγ, IL-12p40, IP-10); TH-2 molecules, including IL-4 and IL-13; Growth factors such as FGF basic; general markers of Inflammation, including myeloperoxidase; and adhesion related molecules, such as ICAM-1.

One of ordinary skill in the art would be able to evaluate the change in expression (or RNA transcription) of one or more of the biomarker panel of SEQ ID NOS:1-10 with appropriate statistical analysis and determine whether the magnitude of change in one or more of the genes/proteins is indicative of a treatment responder to anti-IL-12 therapy, e.g., CNTO 1275, in a Crohn's (or other related disorder) patient; a responder would have a CDAI of greater than or equal to 100. Additionally, the levels of a subjects (patients) pre-treatment, optionally after treatment with a TNFα antagonist, can be compared to a reference standard to predict whether a subject will respond to therapy. Additional methods used to evaluate the biomarker panel to determine or predict responsiveness are described below.

Microarray Data Analysis

Microarray analysis is performed on GeneChip Human Genome U133 Plus 2.0 arrays that allow the analysis of the expression level of more than 47,000 transcripts and variants, including 38,500 well-characterized human genes. RNA amplification, target synthesis and labeling, chip hybridization, washing and staining are performed in accordance with the manufacturer's protocol (Affymetrix, Santa Clara, Calif.). The GeneChips are scanned using the GeneChip Scanner 3000. The data are analyzed with GCOS 1.4 (GeneChip Operating System) using Affymetrix default analysis settings and global scaling as normalization method. The trimmed mean target intensity of each array can be set to 500. Data quality is assessed by hybridization intensity distribution and Pearson's correlation in Partek Pro software version 6.1 (Partek Inc., St. Charles, Mo.).

Using GeneSpring™ software version 7.2 (Agilent Technologies, Palo Alto, Calif.), the intensity for probe set is normalized across all samples. Each measurement is divided by the median of all measurements in that sample. The intensity of a probe set is then normalized to the median intensity of that probe set in the control group. Normalized intensity of probe set A in sample X is calculated as following:

$$\frac{\text{(Signal intensity of probe set A in sample X)}}{\text{(Median intensity of all measurements in sample X)} \times \text{(Median intensity of probe set A across all week-0 samples)}}$$

Using Partek Pro 6.2, statistical analysis identifies significant differences between responders and nonresponders using log-2 transformed normalized intensities. ANOVA is conducted between responders and non-responders, using samples collected at week 0 (prior to treatment). Statistically significant differences are determined after applying a false discovery rate (FDR) of 10% for multiple testing correction.

Classification of CNT01275 responsiveness for each patient sample is generated with the 'K-Nearest Neighbors' algorithm, using GeneSpring™7.2. A classifier containing transcripts showing significant differential expression between responders and non-responders prior to IFX treatment is evaluated by leave-one-out cross-validation for its efficiency of classification. A p-value is calculated to measure the probability that a test sample is predicted as belonging to one class by chance. And a p-value ratio is defined as the p-value of the first best class relative to that of the next best class.

These results are novel findings in that clinical response outcome to CNTO1275 or other anti-IL-12 antibody treatment in moderate to severe Crohn's disease patients can be predicted prior to treatment via assessing gene expression levels of a panel of selective genes. The expression changes in a panel of genes as represented in Tables 1A and 1B can constitute a classifier that serves as a biomarker profile indicative of the response of a subject to treatment at baseline prior to any treatment.

Real Time PCR (TaqMan®) Confirmation:

In order to confirm the microarray finding by an independent means, Real Time PCR (TaqMan®) technology is employed. Two micrograms of total RNA in the volume of 100 μL is converted to cDNA in the presence of MultiScribe Reverse Transcriptase. The reaction is carried out by incubating for 10 minutes at 25° C. followed by 30 minutes at 48° C. Reverse Transcriptase is inactivated at 95° C. for 5 minutes. Twenty-five nanograms of cDNA per reaction are used in real time PCR with ABI 7900 system (Foster City, Calif.). In the presence of AmpliTaq Gold DNA polymerase (ABI biosystem, Foster City, Calif.), the reaction is incubated for 2 minutes at 50° C. followed by 10 minutes at 95° C. Then, the reaction is run for 40 cycles at 15 seconds, at 95° C. and 1 minute, 60° C. per cycle. The housekeeping gene GAPDH (glyceraldehyde-3-phosphate dehydrogenase) is used to normalize gene expression. The TaqMan® results are run to determine the consistency with the observation from the microarray analysis.

Utility of the Response Signature.

The response signature for anti-IL-12 treatment in Crohn's disease described herein can be assessed and used as described below.

1) Colonoscopic biopsy, serum, and/or plasma samples are obtained from lesional sites of patients with active Crohn's (or related diseases and disorders). RNA will then be isolated from the samples and subjected to real time RT-PCR analysis. One microgram of total RNA in the volume of 50 μl is converted to cDNA in the presence of MultiScribe Reverse Transcriptase (ABI biosystem, Foster City, Calif.). The reaction is carried out by incubating for 10 minutes at 25° C. followed by 30 minutes at 48° C. Reverse Transcriptase is inactivated at 95° C.

for 5 minutes. Twenty-five nanograms of cDNA per reaction are used in real time PCR with ABI 7900 system (Foster City, Calif.). In the presence of AmpliTaq Gold DNA polymerase (ABI biosystem, Foster City, Calif.), the reaction is incubated for 2 minutes at 50° C. followed by 10 minutes at 95° C. Then the reaction is run for 40 cycles at 15 seconds, at 95° C. and 1 minute, 60° C. per cycle using primer/probe sets specific for the genes in the response signature. House keeping genes, such as GAPDH or actin, will be used as internal calibrators. The relative change in gene expression is calculated using the delta-delta Ct method described by Applied Biosystems using values in the non-responder samples as the calibrator or comparator.

2) If a similar gene expression profile meets the parameters of the gene profile signature for a type of therapy, i.e., one or more of the 10 signature genes in the profile described above show expression levels predictive of responders in relation to non-responders, the patient is considered a likely treatment responder to the therapy. In which case, the patient will be treated with the therapy.

3) If the gene expression profile does not meet the parameters of the gene profile signature for responder, i.e., lower expression level, then the patient is defined as a likely treatment non-responder. In which case, the patient may not be treated with the therapy. This enables a patient to avoid a type of therapy earlier after being deemed a non-responder. This can allow the patient to receive a different type of therapy.

Comparison Method in Relation to Reference Standard:

Total RNA is to be analyzed on a gene chip array for the expression intensities of the 10-gene panel listed in Table 1A. The following procedures are exemplary of a method of evaluating members of a gene panel of the invention against a reference standard in order to compare values of the gene panel members:

1. Total RNA is extracted from a colonoscopic biopsy, plasma or serum sample from a prospective Crohn's disease (or related disorder) patient before (or during) treatment and the total RNA quantity and quality is assessed as specified above in Example 1.

2. Total RNA is run in duplicate on three separate identical gene chip arrays, e.g., GeneChip Human Genome U133 Plus 2.0 arrays as follows:

a. RNA amplification, target synthesis and labeling, chip hybridization, washing and staining are performed according to the manufacturer's protocol, e.g., Affymetrix, Santa Clara, Calif.

b. The GeneChips are scanned using, e.g., the GeneChip Scanner 3000.

c. The data is analyzed with, e.g., GCOS 1.4 (GeneChip Operating System) using Affymetrix default analysis settings and global scaling as normalization method, with the trimmed mean target intensity of each array set to 500.

d. The data quality is determined by correlating the data of each gene among the duplicates and across the three arrays.

i. A correlation coefficient>0.9 should be achieved.

e. An average intensity value is calculated with a standard error representing the variability.

f. The patient should respond to treatment with an anti-IL-12 antibody (e.g., CNTO1275) if:

i. The average intensity value is equal to or above X for each gene probe set; or ii. The average intensity value for the gene panel is equal to or above X.

g. The patient should not respond to anti-IL-12 antibody (e.g., CNT01275) treatment if:

i. The average intensity value is below Y for each gene probe set; or ii. The average intensity value for the gene panel is below Y.

Although illustrated and described above with reference to certain specific embodiments, the present invention is nevertheless not intended to be limited to the details shown. Rather, the present invention is directed to the Crohn's disease-related genes and gene products. Polynucleotides, antibodies, apparatus, and kits disclosed herein and uses thereof, and methods for predicting responsiveness to treatment and controlling the levels of the Crohn's disease-related biomarker genes, and various modifications may be made in the details within the scope and range of equivalents of the claims and without departing from the spirit of the invention.

What is claimed:

1. A method for predicting the suitability of treatment with an anti-IL-12 antibody therapy for Crohn's disease in a subject, comprising:
   a) preparing a sample of nucleic acids from a specimen obtained from the subject;
   b) contacting the sample with a panel of nucleic acid segments consisting of at least a portion of the nucleotide sequences corresponding to SEQ ID NOS:1-10 to detect levels of the panel segments;
   c) evaluating the sample against a reference standard to determine the magnitude of change in the amounts of the portions of the nucleotide sequences present in the sample;
   d) correlating the magnitude of change with the suitability of treatment with anti-IL-12 antibody therapy for Crohn's disease; and
   e) treating or refraining from treating the subject based on the correlation of suitability of treatment.

2. The method of claim 1, wherein the anti-IL-12 antibody is CNTO1275.

3. The method of claim 1, wherein the reference standard is from a colon biopsy, serum, or plasma from an untreated Crohn's disease patient, a responder to the anti-IL-12 antibody therapy, or a non-responder to the anti-IL-12 antibody therapy.

4. The method of claim 1, wherein the collection is an array of nucleic acid segments.

5. The method of claim 1, wherein the evaluating step comprises evaluating the sample against a reference standard and determining whether the average intensity value for each of the members of the panel is equal to or above X or below Y.

6. The method of claim 5, wherein the average intensity value for each of the members of the panel being equal to or above X indicates the subject will be a responder to the target therapy and the average intensity value for each of the members of the panel being below Y indicates the subject will be a non-responder.

7. The method of claim 1, wherein the sample is from a patient providing the sample prior to administration of a therapy.

8. The method of claim 1, wherein at least one member from the panel is selected from the group consisting of genes for cytokines, chemokines, proteins involved in extracellular matrix remodeling, angiogenesis associated growth factors, a cell adhesion molecule, and a myeloperoxidase.

9. The method of claim 1, wherein the specimen comprises plasma or serum from a subject.

* * * * *

SEQUENCE LISTING

```
<160> NUMBER OF SEQ ID NOS: 10

<210> SEQ ID NO 1
<211> LENGTH: 1207
<212> TYPE: DNA
<213> ORGANISM: Homo sapiens

<400> SEQUENCE: 1

gggggagaca ttcctcaatt gcttagacat attctgagcc tacagcagag gaacctccag      60

tctcagcacc atgaatcaaa ctgccattct gatttgctgc cttatctttc tgactctaag     120

tggcattcaa ggagtacctc tctctagaac tgtacgctgt acctgcatca gcattagtaa     180

tcaacctgtt aatccaaggt ctttagaaaa acttgaaatt attcctgcaa gccaattttg     240

tccacgtgtt gagatcattg ctacaatgaa aaagaagggt gagaagagat gtctgaatcc     300

agaatcgaag gccatcaaga atttactgaa agcagttagc aaggaaaggt ctaaaagatc     360

tccttaaaac cagaggggag caaaatcgat gcagtgcttc caaggatgga ccacacagag     420

gctgcctctc ccatcacttc cctacatgga gtatatgtca agccataatt gttcttagtt     480
```

```
tgcagttaca ctaaaaggtg accaatgatg gtcaccaaat cagctgctac tactcctgta    540

ggaaggttaa tgttcatcat cctaagctat tcagtaataa ctctaccctg gcactataat    600

gtaagctcta ctgaggtgct atgttcttag tggatgttct gaccctgctt caaatatttc    660

cctcaccttt cccatcttcc aagggtacta aggaatcttt ctgctttggg gtttatcaga    720

attctcagaa tctcaaataa ctaaaaggta tgcaatcaaa tctgcttttt aaagaatgct    780

ctttacttca tggacttcca ctgccatcct cccaaggggc ccaaattctt tcagtggcta    840

cctacataca attccaaaca catacaggaa ggtagaaata tctgaaaatg tatgtgtaag    900

tattcttatt taatgaaaga ctgtacaaag tagaagtctt agatgtatat atttcctata    960

ttgttttcag tgtacatgga ataacatgta attaagtact atgtatcaat gagtaacagg   1020

aaaattttaa aaatacagat agatatatgc tctgcatgtt acataagata aatgtgctga   1080

atggttttca aaataaaaat gaggtactct cctggaaata ttaagaaaga ctatctaaat   1140

gttgaaagat caaaaggtta ataaagtaat tataactcaa aaaaaaaaaa aaaaaaaaaa   1200

aaaaaaa                                                             1207
```

<210> SEQ ID NO 2
<211> LENGTH: 661
<212> TYPE: DNA
<213> ORGANISM: Homo sapiens

<400> SEQUENCE: 2

```
tcaaactgaa gctcgcactc tcgcctccag catgaaagtc tctgccgccc ttctgtgcct     60

gctgctcata gcagccacct tcattcccca agggctcgct cagccagatg caatcaatgc    120

cccagtcacc tgctgctata acttcaccaa taggaagatc tcagtgcaga ggctcgcgag    180

ctatagaaga atcaccagca gcaagtgtcc caaagaagct gtgatcttca agaccattgt    240

ggccaaggag atctgtgctg accccaagca gaagtgggtt caggattcca tggaccacct    300

ggacaagcaa acccaaactc cgaagacttg aacactcact ccacaaccca agaatctgca    360

gctaacttat tttcccctag ctttccccag acatcctgtt ttattttatt ataatgaatt    420

ttgtttgttg atgtgaaaca ttatgcctta agtaatgtta attcttattt aagttattga    480

tgttttaagt ttatctttca tggtactagt gttttttaga tacagagact tggggaaatt    540

gcttttcctc ttgaaccaca gttctacccc tgggatgttt tgagggtctt tgcaagaatc    600

atttttttaa cattccaatg catttaatac aaagaattgc taaaatatta ttgtggaaat    660

g                                                                    661
```

<210> SEQ ID NO 3
<211> LENGTH: 4506
<212> TYPE: DNA
<213> ORGANISM: Homo sapiens

<400> SEQUENCE: 3

```
aagcttcaga gccaggcagt tctgggcttg aacactagtt ctgtggatta actcgctctg     60

tgatcacagg caaattcctt aactctctga gccttagttt ccccctctga aaacaggagg    120

gatactcatt aaacttacct tacaggtggt gaggatgaaa cgagaggctt atagagaact    180

tattacggtg cttgacacag taaatctcaa aaaatgcatt attattatta tggttcagag    240

gtaaagtgac ttgcccaagg tcacatagct ggaaaatgca gagccgggat ggaaatccag    300

gacttcgtga cgcaaagcag atgttcattg gttagtgaac tttagaactt caacttttct    360

gtaaaggaag ttaattatct ccatctcaca gtctcattta ttagataagc atataaaatg    420
```

-continued

```
cctggcacat agtaggccct ttaaatacag cttattgggc cgggcgccat gctcatgccc    480
gtaatcctag cactttggga ggccaggtgg gcagatcact tgagtcagaa gttcgaaacc    540
agcctggtca acgtagtgaa accccatctc tactaaaaat acaaaaaatt tagccaggcg    600
tggtggcgca cctataatac cagctactcg ggaggctgag gcaggagaat tgcttgaacc    660
cgggaggcag atgttgcagt gagccgagat cacgccactg cactccagcc tgggtgacag    720
agtgatacta cccccccaa aaataaaata aaataaataa atacaacttt ttgagttgtt    780
agcaggtttt tcccaaatag ggctttgaag aaggtgaata tagaccctgc ccgatgccgg    840
ctggctagga agaaaggagt gagggaggct gctggtgtgg gaggcttggg agggaggctt    900
ggcataagtg tgataattgg gcctggagat ttggctgcat ggaggcaggg ctggaggaac    960
taagggctcc tatagattat ttccccatat cctgccgcaa tttgcagttg aagaatccta   1020
agctgagaaa ggggaggcat ttactccagg ttacactgca gcttagagcc caataacctg   1080
gtttggtgat tccaagttag aatcatggtc ttttggcagg gtctcgctct gttgcccagg   1140
ctggagtgca gtgacataat catggctcac tgtatccttg accttctttc tgggctcaag   1200
caatcctccc acctcggcct cccaaagtgc taagattaca ggaatgagcc accatacctg   1260
gccctgaatc ttgggtcttg gccttagtaa ttaaaaccaa tcaccaccat ccgttgcgga   1320
cttacaacct acagtgttct aaacatttta tatgtttgat ctcatttaat cctcacatca   1380
atttagggac aaagagcccc ccaccccccg tttttttttt tacagctgag gaaacacttc   1440
aaagtggtaa gacatttgcc cgaggtcctg aaggaagaga gtaaagccat gtctgctgtt   1500
ttctagaggc tgctactgtc ccctttactg ccctgaagat tcagcctgcg gaagacaggg   1560
ggttgcccca gtggaattcc ccagccttgc ctagcagagc ccattccttc cgcccccaga   1620
tgaagcaggg agaggaagct gagtcaaaga aggctgtcag ggagggaaaa agaggacaga   1680
gcctggagtg tggggagggg tttggggagg atatctgacc tgggaggggg tgttgcaaaa   1740
ggccaaggat gggccagggg gatcattagt ttcagaaaga agtctcaggg agtcttccat   1800
cactttccct tggctgacca ctggaggctt tcagaccaag ggatgggggga tccctccagc   1860
ttcatccccc tccctccctt tcatacagtt cccacaagct ctgcagtttg caaaacccta   1920
cccctcccct gagggcctgc ggtttcctgc gggtctgggg tcttgcctga cttggcagtg   1980
gagactgcgg gcagtggaga gaggaggagg tggtgtaagc cctttctcat gctggtgctg   2040
ccacacacac acacacacac acacacacac acacacacac acaccctgac ccctgagtca   2100
gcacttgcct gtcaaggagg ggtggggtca caggagcgcc tccttaaagc ccccacaaca   2160
gcagctgcag tcagacacct ctgccctcac catgagcctc tggcagcccc tggtcctggt   2220
gctcctggtg ctgggctgct gctttgctgc ccccagacag cgccagtcca cccttgtgct   2280
cttccctgga gacctgagaa ccaatctcac cgacaggcag ctggcagagg aatacctgta   2340
ccgctatggt tacactcggg tggcagagat gcgtggagag tcgaaatctc tggggcctgc   2400
gctgctgctt ctccagaagc aactgtccct gcccgagacc ggtgagctgg atagcgccac   2460
gctgaaggcc atgcgaaccc cacggtgcgg ggtcccagac ctgggcagat tccaaacctt   2520
tgagggcgac ctcaagtggc accaccacaa catcacctat tggatccaaa actactcgga   2580
agacttgccg cgggcggtga ttgacgacgc ctttgcccgc gccttcgcac tgtggagcgc   2640
ggtgacgccg ctcaccttca ctcgcgtgta cagccgggac gcagacatcg tcatccagtt   2700
tggtgtcgcg gagcacggag acgggtatcc cttcgacggg aaggacgggc tcctggcaca   2760
cgcctttcct cctggccccg gcattcaggg agacgcccat ttcgacgatg acgagttgtg   2820
```

```
gtccctgggc aagggcgtcg tggttccaac tcggtttgga aacgcagatg gcgcggcctg   2880
ccacttcccc ttcatcttcg agggccgctc ctactctgcc tgcaccaccg acggtcgctc   2940
cgacggcttg ccctggtgca gtaccacggc caactacgac accgacgacc ggtttggctt   3000
ctgccccagc gagagactct acacccggga cggcaatgct gatgggaaac cctgccagtt   3060
tccattcatc ttccaaggcc aatcctactc cgcctgcacc acggacggtc gctccgacgg   3120
ctaccgctgg tgcgccacca ccgccaacta cgaccgggac aagctcttcg gcttctgccc   3180
gacccgagct gactcgacgg tgatgggggg caactcggcg gggagctgt gcgtcttccc    3240
cttcactttc ctgggtaagg agtactcgac ctgtaccagc gagggccgcg gagatgggcg   3300
cctctggtgc gctaccacct cgaactttga cagcgacaag aagtggggct tctgcccgga   3360
ccaaggatac agtttgttcc tcgtggcggc gcatgagttc ggccacgcgc tgggcttaga   3420
tcattcctca gtgccggagg cgctcatgta ccctatgtac cgcttcactg aggggccccc   3480
cttgcataag gacgacgtga atggcatccg gcacctctat ggtcctcgcc ctgaacctga   3540
gccacggcct ccaaccacca ccacaccgca gcccacggct cccccgacgg tctgccccac   3600
cggacccccc actgtccacc cctcagagcg ccccacagct ggccccacag gtccccccctc  3660
agctggcccc acaggtcccc ccactgctgg cccttctacg gccactactg tgcctttgag   3720
tccggtggac gatgcctgca acgtgaacat cttcgacgcc atcgcggaga ttgggaacca   3780
gctgtatttg ttcaaggatg ggaagtactg gcgattctct gagggcaggg ggagccggcc   3840
gcagggcccc ttccttatcg ccgacaagtg gcccgcgctg ccccgcaagc tggactcggt   3900
ctttgaggag ccgctctcca agaagctttt cttcttctct gggcgccagg tgtgggtgta   3960
cacaggcgcg tcggtgctgg gcccgaggcg tctggacaag ctgggcctgg gagccgacgt   4020
ggcccaggtg accggggccc tccggagtgg caggggggaag atgctgctgt tcagcgggcg  4080
gcgcctctgg aggttcgacg tgaaggcgca gatggtggat ccccggagcg ccagcgaggt   4140
ggaccggatg ttccccgggg tgcctttgga cacgcacgac gtcttccagt accgagagaa   4200
agcctatttc tgccaggacc gcttctactg gcgcgtgagt tcccggagtg agttgaacca   4260
ggtggaccaa gtgggctacg tgacctatga catcctgcag tgccctgagg actagggctc   4320
ccgtcctgct ttgcagtgcc atgtaaatcc ccactgggac caaccctggg gaaggagcca   4380
gtttgccgga tacaaactgg tattctgttc tggaggaaag ggaggagtgg aggtgggctg   4440
ggccctctct tctcaccttt gtttttgtt ggagtgtttc taataaactt ggattctcta    4500
accttt                                                               4506
```

```
<210> SEQ ID NO 4
<211> LENGTH: 3634
<212> TYPE: DNA
<213> ORGANISM: Homo sapiens

<400> SEQUENCE: 4

gaattccggg tgatttcact cccggctgtc caggcttgtc ctgctacccc acccagcctt     60
tcctgaggcc tcaagcctgc caccaagccc ccagctcctt ctccccgcag gacccaaaca    120
caggcctcag gactcaacac agcttttccc tccaacccgt ttctctccc tcaacggact     180
cagctttctg aagcccctcc cagttctagt tctatctttt tcctgcatcc tgtctggaag    240
ttagaaggaa acagaccaca gacctggtcc ccaaaagaaa tggaggcaat aggttttgag    300
gggcatgggg acggggttca gcctccaggg tcctacacac aaatcagtca gtggcccaga    360
agaccccccct cggaatcgga gcagggagga tggggagtgt gaggggtatc cttgatgctt   420
```

```
gtgtgtcccc aactttccaa atccccgccc ccgcgatgga gaagaaaccg agacagaagg    480
tgcagggccc actaccgctt cctccagatg agctcatggg tttctccacc aaggaagttt    540
tccgctggtt gaatgattct ttccccgccc tcctctcgcc ccagggacat ataaaggcag    600
ttgttggcac acccagccag cagacgctcc ctcagcaagg acagcagagg accagctaag    660
agggagagaa gcaactacag acccccccctg aaaacaaccc tcagacgcca catcccctga    720
caagctgcca ggcaggttct cttcctctca catactgacc cacggcttca ccctctctcc    780
cctggaaagg acaccatgag cactgaaagc atgatccggg acgtggagct ggccgaggag    840
gcgctcccca agaagacagg ggggccccag ggctccaggc ggtgcttgtt cctcagcctc    900
ttctccttcc tgatcgtggc aggcgccacc acgctcttct gcctgctgca ctttggagtg    960
atcggccccc agagggaaga ggtgagtgcc tggccagcct tcatccactc tcccacccaa   1020
ggggaaatga gagacgcaag agagggagag agatgggatg ggtgaaagat gtgcgctgat   1080
agggagggat gagagagaaa aaaacatgga gaaagacggg gatgcagaaa gagatgtggc   1140
aagagatggg gaagagagag agagaaagat ggagagacag gatgtctggc acatggaagg   1200
tgctcactaa gtgtgtatgg agtgaatgaa tgaatgaatg aatgaacaag cagatatata   1260
aataagatat ggagacagat gtggggtgtg agaagagaga tgggggaaga aacaagtgat   1320
atgaataaag atggtgagac agaaagagcg ggaaatatga cagctaagga gagagatggg   1380
ggagataagg agagaagaag atagggtgtc tggcacacag aagacactca gggaaagagc   1440
tgttgaatgc tggaaggtga atacacagat gaatggagag agaaaaccag acacctcagg   1500
gctaagagcg caggccagac aggcagccag ctgttcctcc tttaagggtg actccctcga   1560
tgttaaccat tctccttctc cccaacagtt ccccagggac ctctctctaa tcagccctct   1620
ggcccaggca gtcagtaagt gtctccaaac ctctttccta attctgggtt tgggtttggg   1680
ggtagggtta gtaccggtat ggaagcagtg gggaaaattt aaagttttgg tcttgggga    1740
ggatggatgg aggtgaaagt agggggtat tttctaggaa gtttaagggt ctcagctttt    1800
tcttttctct ctcctcttca ggatcatctt ctcgaacccc gagtgacaag cctgtagccc   1860
atgttgtagg taagagctct gaggatgtgt cttggaactt ggagggctag gatttgggga   1920
ttgaagcccg gctgatggta ggcagaactt ggagacaatg tgagaaggac tcgctgagct   1980
caagggaagg gtggaggaac agcacaggcc ttagtgggat actcagaacg tcatggccag   2040
gtgggatgtg ggatgacaga cagagaggac aggaaccgga tgtggggtgg gcagagctcg   2100
agggccagga tgtggagagt gaaccgacat ggccacactg actctcctct ccctctctcc   2160
ctccctccag caaaccctca agctgagggg cagctccagt ggctgaaccg ccgggccaat   2220
gccctcctgg ccaatggcgt ggagctgaga gataaccagc tggtggtgcc atcagagggc   2280
ctgtacctca tctactccca ggtcctcttc aagggccaag gctgcccctc cacccatgtg   2340
ctcctcaccc acaccatcag ccgcatcgcc gtctcctacc agaccaaggt caacctcctc   2400
tctgccatca agagcccctg ccagagggag accccagagg gggctgaggc caagccctgg   2460
tatgagccca tctatctggg aggggtcttc cagctggaga agggtgaccg actcagcgct   2520
gagatcaatc ggcccgacta tctcgacttt gccgagtctg ggcaggtcta ctttgggatc   2580
attgccctgt gaggaggacg aacatccaac cttcccaaac gcctcccctg ccccaatccc   2640
tttattaccc cctccttcag acaccctcaa cctcttctgg ctcaaaaaga gaattggggg   2700
cttagggtcg gaacccaagc ttagaacttt aagcaacaag accaccactt cgaaacctgg   2760
gattcaggaa tgtgtggcct gcacagtgaa gtgctggcaa ccactaagaa ttcaaactgg   2820
```

```
ggcctccaga actcactggg gcctacagct ttgatccctg acatctggaa tctggagacc   2880

agggagcctt tggttctggc cagaatgctg caggacttga gaagacctca cctagaaatt   2940

gacacaagtg gaccttaggc cttcctctct ccagatgttt ccagacttcc ttgagacacg   3000

gagcccagcc ctccccatgg agccagctcc ctctatttat gtttgcactt gtgattattt   3060

attatttatt tattatttat ttatttacag atgaatgtat ttatttggga gaccggggta   3120

tcctggggga cccaatgtag gagctgcctt ggctcagaca tgttttccgt gaaaacggag   3180

ctgaacaata ggctgttccc atgtagcccc ctggcctctg tgccttcttt tgattatgtt   3240

ttttaaaata tttatctgat taagttgtct aaacaatgct gatttggtga ccaactgtca   3300

ctcattgctg agcctctgct ccccagggga gttgtgtctg taatcgccct actattcagt   3360

ggcgagaaat aaagtttgct tagaaaagaa acatggtctc cttcttggaa ttaattctgc   3420

atctgcctct tcttgtgggt gggaagaagc tccctaagtc ctctctccac aggctttaag   3480

atccctcgga cccagtccca tccttagact cctagggccc tggagaccct acataaacaa   3540

agcccaacag aatattcccc atcccccagg aaacaagagc ctgaacctaa ttacctctcc   3600

ctcagggcat gggaatttcc aactctggga attc                               3634
```

<210> SEQ ID NO 5
<211> LENGTH: 159
<212> TYPE: DNA
<213> ORGANISM: Homo sapiens

<400> SEQUENCE: 5

```
aatagtgact ctgaatgtcc cctgtcccac gatgggtact gcctccatga tggtgtgtgc     60

atgtatattg aagcattgga caagtatgca tgcaactgtg ttgttggcta catcggggag    120

cgatgtcagt accgagacct gaagtggtgg gaactgcgc                           159
```

<210> SEQ ID NO 6
<211> LENGTH: 1131
<212> TYPE: DNA
<213> ORGANISM: Homo sapiens

<400> SEQUENCE: 6

```
cattctgccc tcgagcccac cgggaacgaa agagaagctc tatctcccct ccaggagccc     60

agctatgaac tccttctcca caagcgcctt cggtccagtt gccttctccc tggggctgct    120

cctggtgttg cctgctgcct tccctgcccc agtacccccca ggagaagatt ccaaagatgt    180

agccgcccca cacagacagc cactcacctc ttcagaacga attgacaaac aaattcggta    240

catcctcgac ggcatctcag ccctgagaaa ggagacatgt aacaagagta acatgtgtga    300

aagcagcaaa gaggcactgg cagaaaacaa cctgaacctt ccaaagatgg ctgaaaaaga    360

tggatgcttc caatctggat tcaatgagga gacttgcctg gtgaaaatca tcactggtct    420

tttggagttt gaggtatacc tagagtacct ccagaacaga tttgagagta gtgaggaaca    480

agccagagct gtgcagatga gtacaaaagt cctgatccag ttcctgcaga aaaaggcaaa    540

gaatctagat gcaataacca cccctgaccc aaccacaaat gccagcctgc tgacgaagct    600

gcaggcacag aaccagtggc tgcaggacat gacaactcat ctcattctgc gcagctttaa    660

ggagttcctg cagtccagcc tgagggctct tcggcaaatg tagcatgggc acctcagatt    720

gttgttgtta atgggcattc cttcttctgg tcagaaacct gtccactggg cacagaactt    780

atgttgttct ctatggagaa ctaaaagtat gagcgttagg acactatttt aattattttt    840

aatttattaa tatttaaata tgtgaagctg agttaattta tgtaagtcat atttatattt    900
```

ttaagaagta ccacttgaaa cattttatgt attagttttg aaataataat ggaaagtggc 960
tatgcagttt gaatatcctt tgtttcagag ccagatcatt tcttggaaag tgtaggctta 1020
cctcaaataa atggctaact tatacatatt tttaaagaaa tatttatatt gtatttatat 1080
aatgtataaa tggtttttat accaataaat ggcattttaa aaaattcagc a 1131

<210> SEQ ID NO 7
<211> LENGTH: 1173
<212> TYPE: DNA
<213> ORGANISM: Homo sapiens

<400> SEQUENCE: 7
cggcacgagc acagtgctcc ggatcctcca atcttcgctc ctccaatctc cgctcctcca 60
cccagttcag gaacccgcga ccgctcgcag cgctctcttg accactatga gcctcctgtc 120
cagccgcgcg gcccgtgtcc ccggtccttc gagctccttg tgcgcgctgt tggtgctgct 180
gctgctgctg acgcagccag ggcccatcgc cagcgctggt cctgccgctg ctgtgttgag 240
agagctgcgt tgcgtttgtt tacagaccac gcagggagtt catcccaaaa tgatcagtaa 300
tctgcaagtg ttcgccatag gcccacagtg ctccaaggtg gaagtggtag cctccctgaa 360
gaacgggaag gaaatttgtc ttgatccaga agcccctttt ctaaagaaag tcatccagaa 420
aattttggac ggtggaaaca aggaaaactg attaagagaa atgagcacgc atggaaaagt 480
ttcccagtct acagcagaga agttttctgg aggtctctga acccagggaa gacaagaagg 540
aaagattttg ttgttgtttg tttatttggt ttccccagta gttagctttc ttccctggat 600
tcctcacttt tgaagagtgt gaggaaaacc tatgtttggc gcttaagctt tcagctcagc 660
ttaatgaagt gtttagcata gtacctctgc tatttgctgt tattttatct gctatgctat 720
tgaagttttg gcaattgact atagtgtgag ccaggaatca ctggctgtta atcttacaaa 780
gtgtcttgga attgtaggtg actattattt ttccaagaaa tatcccttaa gatattaact 840
gagaaggctg gggtttaat gtggaaatga tgtttcaaaa ggaatcctgt gatggaaata 900
caactggtat cttcactttt ttaggaattg ggaaatattt taatgtttct tggggaatat 960
gttagagaat tcccttactc ttgattgtgg gatactattt aattatttca ctttagaaag 1020
ctgagtgttt cacaccttat ctatgtagaa tatatttcct tattcagaat ttctaaaagt 1080
ttaagttcta tgagggctaa tatcttatct tcctataatt ttagacattg ctttaacttt 1140
ttagtaaaaa aaaaaaaaaa aaaaaaaaaa aaa 1173

<210> SEQ ID NO 8
<211> LENGTH: 2568
<212> TYPE: DNA
<213> ORGANISM: Homo sapiens

<400> SEQUENCE: 8
gtccttggaa gctggatgac agcagctggc aaggggataa gagagcagtg agcccctccc 60
tcaaggaggt ctggctttat ccatagacag ggccctctga ggtggggctg aggtacaaag 120
ggggattgag cagcccagga gaagagagat gggggttccc ttcttctctt ctctcagatg 180
catggtggac ttaggacctt gctgggctgg gggtctcact gcagagatga agctgcttct 240
ggccctagca gggctcctgg ccattctggc cacgccccag ccctctgaag gtgctgctcc 300
agctgtcctg gggggaggtgg acacctcgtt ggtgctgagc tccatggagg aggccaagca 360
gctggtggac aaggcctaca aggagcggcg ggaaagcatc aagcagcggc ttcgcagcgg 420
ctcagccagc cccatggaac tcctatccta cttcaagcag ccggtggcag ccaccaggac 480

```
ggcggtgagg gccgctgact acctgcacgt ggctctagac ctgctggaga ggaagctgcg    540

gtccctgtgg cgaaggccat tcaatgtcac tgatgtgctg acgcccgccc agctgaatgt    600

gttgtccaag tcaagcggct gcgcctacca ggacgtgggg gtgacttgcc cggagcagga    660

caaataccgc accatcaccg ggatgtgcaa caacagacgc agccccacgc tgggggcctc    720

caaccgtgcc tttgtgcgct ggctgccggc ggagtatgag gacggcttct ctcttcccta    780

cggctggacg cccggggtca agcgcaacgg cttcccggtg gctctggctc gcgcggtctc    840

caacgagatc gtgcgcttcc ccactgatca gctgactccg gaccaggagc gctcactcat    900

gttcatgcaa tggggccagc tgttggacca cgacctcgac ttcacccctg agccggccgc    960

ccgggcctcc ttcgtcactg gcgtcaactg cgagaccagc tgcgttcagc agccgccctg   1020

cttcccgctc aagatcccgc ccaatgaccc ccgcatcaag aaccaagccg actgcatccc   1080

gttcttccgc tcctgcccgg cttgccccgg gagcaacatc accatccgca accagatcaa   1140

cgcgctcact tccttcgtgg acgccagcat ggtgtacggc agcgaggagc cctggccag    1200

gaacctgcgc aacatgtcca accagctggg gctgctggcc gtcaaccagc gcttccaaga   1260

caacggccgg gccctgctgc cctttgacaa cctgcacgat gacccctgtc tcctcaccaa   1320

ccgctcagcg cgcatcccct gcttcctggc aggggacacc cgttccagtg agatgcccga   1380

gctcacctcc atgcacaccc tcttacttcg ggagcacaac cggctggcca cagagctcaa   1440

gagcctgaac cctaggtggg atggggagag gctctaccag gaagcccgga agatcgtggg   1500

ggccatggtc cagatcatca cttaccggga ctacctgccc ctggtgctgg ggccaacggc   1560

catgaggaag tacctgccca cgtaccgttc ctacaatgac tcagtggacc cacgcatcgc   1620

caacgtcttc accaatgcct tccgctacgg ccacaccctc atccaaccct tcatgttccg   1680

cctggacaat cggtaccagc ccatggaacc caacccccgt gtcccccctca gcagggtctt  1740

ttttgcctcc tggagggtcg tgctggaagg tggcattgac cccatcctcc ggggcctcat   1800

ggccacccct gccaagctga atcgtcagaa ccaaattgca gtggatgaga tccgggagcg   1860

attgtttgag caggtcatga ggattgggct ggacctgcct gctctgaaca tgcagcgcag   1920

cagggaccac ggcctcccag gatacaatgc ctggaggcgc ttctgtgggc tcccgcagcc   1980

tgaaactgtg ggccagctgg gcacggtgct gaggaacctg aaattggcga ggaaactgat   2040

ggagcagtat ggcacgccca acaacatcga catctggatg ggcggcgtgt ccgagcctct   2100

gaagcgcaaa ggccgcgtgg gcccactcct cgcctgcatc atcggtaccc agttcaggaa   2160

gctccgggat ggtgatcggt tttggtggga gaacgagggt gtgttcagca tgcagcagcg   2220

acaggccctg gcccagatct cattgccccg gatcatctgc gacaacacag gcatcaccac   2280

cgtgtctaag aacaacatct tcatgtccaa ctcatatccc cgggactttg tcaactgcag   2340

tacacttcct gcattgaacc tggcttcctg gagggaagcc tcctagaggc caggtaaggg   2400

ggtgcagcag tgaggggtat atctgggctg gccagttgga accacggaga tctccttgcc   2460

ctagatgagc ccagccctgt tctgggtgca gctgagaaaa tgagtgacta gacgttcatt   2520

tgtgtgctca tgtatgtgcg aagtatataa attggctttt catgcgtg                2568
```

```
<210> SEQ ID NO 9
<211> LENGTH: 279
<212> TYPE: DNA
<213> ORGANISM: Homo sapiens

<400> SEQUENCE: 9

atgaagctct gcgtgactgt cctgtctctc ctcatgctag tagctgcctt ctgctctcca     60
```

-continued

```
gcgctctcag caccaatggg ctcagaccct cccaccgcct gctgcttttc ttacaccgcg    120

aggaagcttc ctcgcaactt tgtggtagat tactatgaga ccagcagcct ctgctcccag    180

ccagctgtgg tattccaaac caaaagaagc aagcaagtct gtgctgatcc cagtgaatcc    240

tgggtccagg agtacgtgta tgacctggaa ctgaactga                           279


<210> SEQ ID NO 10
<211> LENGTH: 649
<212> TYPE: DNA
<213> ORGANISM: Homo sapiens

<400> SEQUENCE: 10

tcgggcctcc gaaaccatga actttctgct gtcttgggtg cattggagcc ttgccttgct     60

gctctacctc caccatgcca agtggtccca ggctgcaccc atggcagaag gaggagggca    120

gaatcatcac gaagtggtga agttcatgga tgtctatcag cgcagctact gccatccaat    180

cgagaccctg gtggacatct tccaggagta ccctgatgag atcgagtaca tcttcaagcc    240

atcctgtgtg cccctgatgc gatgcggggg ctgctgcaat gacgagggcc tggagtgtgt    300

gcccactgag gagtccaaca tcaccatgca gattatgcgg atcaaacctc accaaggcca    360

gcacatagga gagatgagct tcctacagca caacaaatgt gaatgcagac caaagaaaga    420

tagagcaaga caagaaaatc cctgtgggcc ttgctcagag cggagaaagc atttgtttgt    480

acaagatccg cagacgtgta aatgttcctg caaaaacaca gactcgcgtt gcaaggcgag    540

gcagcttgag ttaaacgaac gtacttgcag atgtgacaag ccgaggcggt gagccgggca    600

ggaggaagga gcctccctca gcgtttcggg aaccagatct ctcaccagg                649
```